United States Patent
Zikeli et al.

(10) Patent No.: US 11,091,453 B2
(45) Date of Patent: Aug. 17, 2021

(54) PRODUCTION OF AN AMINE OXIDE BY OXIDATION OF A TERTIARY AMINE

(71) Applicant: AUROTEC GMBH, Regau (AT)

(72) Inventors: Stefan Zikeli, Regau (AT); Hannes Kitzler, Lenzing (AT); Verena Fosodeder, Neukirchen an der Vöckla (AT); Tobias Baumeister, Mannheim (DE)

(73) Assignee: AUROTEC GMBH, Regau (AT)

( * ) Notice: Subject to any disclaimer, the term of this patent is extended or adjusted under 35 U.S.C. 154(b) by 9 days.

(21) Appl. No.: 16/343,648

(22) PCT Filed: Dec. 22, 2017

(86) PCT No.: PCT/EP2017/084391
§ 371 (c)(1),
(2) Date: Apr. 19, 2019

(87) PCT Pub. No.: WO2018/115443
PCT Pub. Date: Jun. 28, 2018

(65) Prior Publication Data
US 2019/0300493 A1 Oct. 3, 2019

(30) Foreign Application Priority Data

Dec. 23, 2016 (EP) .................................... 16206623

(51) Int. Cl.
| | | |
|---|---|---|
| *C07D 295/24* | (2006.01) | |
| *C07C 291/04* | (2006.01) | |
| *B01J 19/00* | (2006.01) | |
| *B01J 19/02* | (2006.01) | |
| *B01J 19/24* | (2006.01) | |
| *C08B 1/00* | (2006.01) | |

(52) U.S. Cl.
CPC ........ *C07D 295/24* (2013.01); *B01J 19/0093* (2013.01); *B01J 19/02* (2013.01); *B01J 19/2415* (2013.01); *C07C 291/04* (2013.01); *C08B 1/003* (2013.01)

(58) Field of Classification Search
CPC ............................ C07D 294/24; C07C 291/04
See application file for complete search history.

(56) References Cited

U.S. PATENT DOCUMENTS

| | | | |
|---|---|---|---|
| 2,179,181 A | | 11/1939 | Graenacher et al. |
| 3,215,741 A | * | 11/1965 | Chadwick |
| 3,447,939 A | | 6/1969 | Johnson |
| 4,247,480 A | | 1/1981 | Murata et al. |
| 4,748,241 A | | 5/1988 | Scholten et al. |
| 4,994,614 A | | 2/1991 | Bauer et al. |
| 5,118,423 A | | 6/1992 | Astegger et al. |
| 5,216,154 A | | 6/1993 | Zimmerman |
| 2003/0078424 A1 | | 4/2003 | Wurzinger et al. |
| 2011/0224463 A1 | | 9/2011 | Zikeli et al. |
| 2014/0367896 A1 | | 12/2014 | Zikeli et al. |

FOREIGN PATENT DOCUMENTS

| | | |
|---|---|---|
| DE | 246997 A1 | 8/1910 |
| DE | 3504899 A1 | 8/1986 |
| EP | 0307184 A2 | 3/1989 |
| GB | 153199 A | 1/1979 |

OTHER PUBLICATIONS

European Search Report from European Patent Application No. 16206623.7, dated Jun. 21, 2017.
International Search Report from International Patent Application No. PCT/EP2017/084391, dated Feb. 27, 2018.
Hessel et al., "Micro Process Engineering—vol. 1: Fundamentals, Operations and Catalysts", Wiley Publishing, Apr. 11, 2013, pp. 3-21.
Hoffmann et al., "Combination of Anaerobic Treatment and Nutrient Removal of Wastewater in Brazil", Jan. 2002, pp. 1-8.
Margesin et al., "Praxis der Biotechnologischen Absluftreinigung", Springer Publishing, 1996 ed., pp. 29-37, 119, 120, 122-125.
Némethné-Sóvágó et al., "Microreactors: A New Concept for Chemical Synthesis and Technological Feasibility", Materials Science and Engineering (2014), 39(2), pp. 89-101.
Office Action received in Chinese Application No. 201710086280.6 dated Apr. 6, 2021. (English Translation).

* cited by examiner

*Primary Examiner* — Matthew P Coughlin
(74) *Attorney, Agent, or Firm* — Greer, Burns & Crain, Ltd.

(57) ABSTRACT

A method for producing an amine oxide by oxidation of a tertiary amine in a reactor under continuous introduction of tertiary amine in a reaction fluid and export of amine oxide, wherein a suitable surface-to-volume ratio and/or a suitable flow speed with corresponding surface/volume loads are selected in the continuous process. The reaction fluid is usually reacted in the reactor with a laminar flow.

20 Claims, 7 Drawing Sheets

PRODUCTION OF AN AMINE OXIDE BY OXIDATION OF A TERTIARY AMINE

The present invention relates to the field of oxidation of tertiary amines to form amine oxides.

BACKGROUND

Cellulose can be dissolved in aqueous solutions of amine oxides, for example solutions of N-methylmorpholine N-oxide (NMMO or NMMNO), in order to produce spinning products, such as filaments, staple fibres, films, etc., from the obtained spinning solution (WO 2013/030400, U.S. Pat. Nos. 2,179,181, 3,447,939). There is thus a growing need for amine oxides such as NMMO. Further applications of tertiary amine oxides are surface-active agents, bacteriostatic agents, shampoos and detergents.

DE 2557456 A1 describes a method for producing amine oxides, wherein a tertiary amine is reacted with hydrogen peroxide in the presence of water. At an amine oxide concentration of more than 30%, the viscosity of the product increases considerably, whereby further processing is hindered. It was found that a viscosity minimum was reached with amine oxide concentration above 60%.

U.S. Pat. No. 3,447,939 describes the discontinuously operated batch production of N-methylmorpholine N-oxides (NMMONO), wherein the reactant N-methylmorpholine (NMM) is reacted in the presence of water and 35% hydrogen peroxide at the selected reaction temperatures of 67-72° C. over a period of time of 4-5 hours to form the corresponding tertiary amine oxide NMMNO. The excess hydrogen peroxide is broken down enzymatically with catalase. The formed reaction product was purified by azeotropic benzene-water distillation and recrystallisation.

In DD 246997 A1 a similar batch method is described, in which hydrogen peroxide (45-50%) is introduced into the reactant NMM via a spraying disc or an injection device in finely dispersed form under vigorous agitation.

In the method according to DE 3618352 A1 any peroxide remaining after an oxidation by means of hydrogen peroxide over 4-6 hours is broken down by catalase.

EP 0 307 184 A2, with reference to U.S. Pat. No. 4,247,480, concerns the problem of nitrosamine formation during the reaction of tertiary amine to form the corresponding amine oxide, and proposes that, with use of a carbon dioxide atmosphere (0.03-3 MPa), the reaction should be performed at low temperatures <45° C. and normal pressure.

Since the nitrosamine formation can also be influenced by nitrogen oxides in the air, which are ubiquitous, U.S. Pat. No. 4,994,614 A proposes exposing the unfilled space of the reaction tank to carbon dioxide so that the nitrogen oxides in the air are kept away. A flushing and exposure measure of this kind is very complex, since the reaction containers must be flushed with or exposed to carbon dioxide before the addition of the reactants, during the reaction, after the reaction and during the emptying of the containers.

U.S. Pat. No. 5,216,154 A proposes, in order to reduce the formation of nitrosamines, that the conversion of tertiary N-methylmorpholine (NMM) into NMMNO should be performed in the stirring tank, with a specific reactant mixture composition and special method parameters.

DE 12 21 645 B describes an oxidation of tertiary amines in a discontinuous process. Incidentally, a continuous oxidation with turbulent process control is mentioned.

The objective of the present invention is to provide a scalable process for producing amine oxides which enables a high yield, low to no by-products and degradation products, and efficient conversion.

SUMMARY

The present invention relates to a method for producing an amine oxide by oxidation of a tertiary amine in a reactor with one or more elongate hollow bodies as reaction region, for example a tube, wherein the reactor is preferably a reaction tube, under continuous introduction of tertiary amine in a reaction fluid and export of amine oxide. To this end, suitable process parameters, in particular a suitable surface-to-volume ratio or an appropriate flow velocity with corresponding surface/volume loads are selected in the continuous process. In particular, i) a surface-to-volume ratio of $0.5$ $m^2/m^3$ or more—at least over a length of the hollow body in which the amine is oxidised to an extent of 50%, ii) a specific surface load of 1 $l/m^2h$ to 40 $l/m^2h$, and/or iii) a specific volume load of 1,000 $l/m^3h$ to 30,000 $l/m^3h$ are/is provided in the hollow body. These three characteristics i), ii) and iii) relate fundamentally to alternative definitions which can describe the method according to the invention. In some embodiments all parameters i), ii) and iii) are applicable. The following detailed description and in particular the preferred embodiments relate to all three parameters i), ii) and iii) equally. All embodiments and aspects according to the invention can be combined with one another, and indeed were, as presented in the experimental examples.

DETAILED DESCRIPTION

Figure 1:
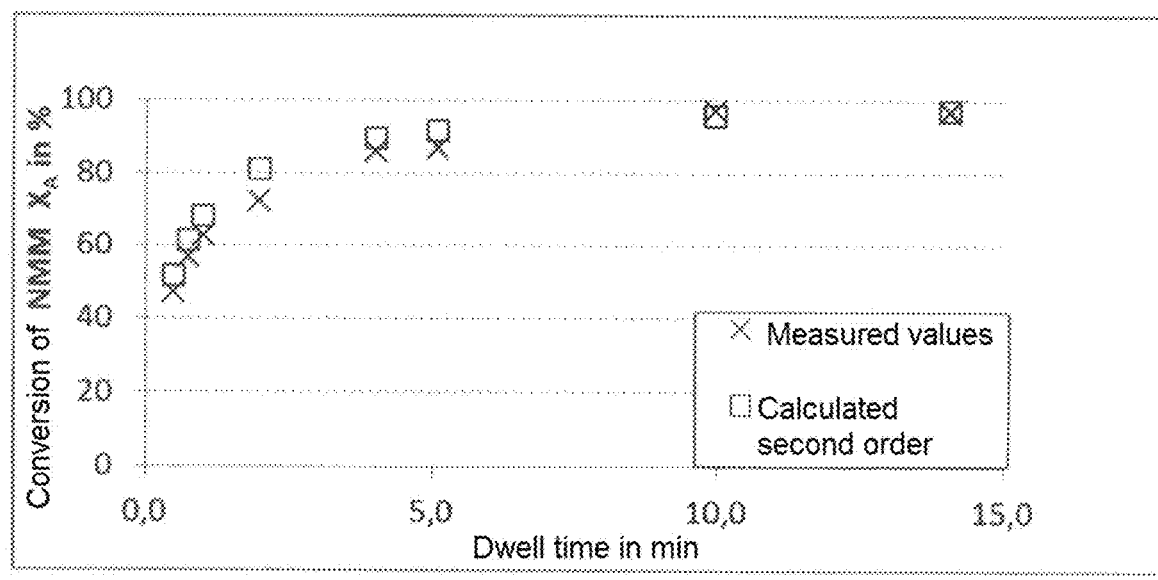
FIG. 1 shows the relationship of residence time in the hollow body and conversion for the case of oxidation of NMM.

The invention relates to a method for producing an amine oxide by oxidation of a tertiary amine in a reactor under continuous introduction of tertiary amine in a reaction fluid and export of amine oxide, wherein a suitable surface-to-volume ratio and/or an appropriate flow velocity with corresponding surface/volume loads are/is selected in the continuous process. The continuous process is performed in an elongate hollow body, with an elongate region between an inlet and outlet. The parameters and structural features according to the invention are disposed between the inlet and outlet, that is to say in the reaction or reactor zone. The reactor is in particular a milli- or micro-structured reactor or apparatus. The hollow body is in particular preferably a tube. In particular, i) a surface-to-volume ratio of 0.5 $m^2/m^3$ or more—at least over a length of the hollow body in which the amine is oxidised to an extent of 50%, ii) a specific surface load of 1 $l/m^2h$ to 40 $l/m^2h$, and/or iii) a specific volume load of 1,000 $l/m^3h$ to 30,000 $l/m^3h$ are/is provided in the hollow body.

Previously, tertiary amine oxides were produced for smaller amounts in a laboratory or for larger amounts in batch processes. An objective for large-scale plants is to be able to use a method that is continuous to the greatest possible extent, since this permits a more efficient execution of the reaction and higher productivity levels on account of shorter downtime periods, since unnecessary cleaning steps before the next batch process are avoided as a result. It has additionally been found that inert gases ($CO_2$) are necessary in batch processes and must be provided together with the reaction fluid. In the milli- or micro-structured apparatus according to the invention, this problem is eradicated, since the inert gas can be introduced directly into the tubes without creation of a gas region or without a gas region posing a danger. In accordance with the invention both pressure and temperature can be better controlled.

In addition, it is possible in a continuous reactor to divide the continuously moved reaction fluid into individual regions, in which the reaction is at different stages of progression. These regions may be treated differently in respect of pressure and/or temperature or temperature control. Such regions are in particular the first region, in which up to 50% (mol %) of the tertiary amine is oxidised (quick reaction, strong exothermic nature) and the second region, in which the rest of the tertiary amine (apart from the desired yield) is oxidised (lower reaction, lesser exothermic nature).

The term "continuous" reaction or process control means that starting material, that is to say fluid containing the tertiary amine, is fed continually during the reaction and is then oxidised continually in the reactor. The term "continually" does not mean that the process may not be stopped, but merely that during the production of amine oxide the reactants are fed more or less uniformly. The continuous feed is preferably interrupted during the oxidation reaction. Alternatively, but less preferably, a batchwise and/or periodic feed can also be selected. That said with regard to the feed also applies for a discharge of the product, i.e. the amine oxide.

The reactor is usually a milli- or micro-structured apparatus and/or a reactor with an elongate hollow body as reaction body, preferably a tubular microreactor. A suitable microreactor is disclosed for example in WO 2010/055034 (incorporated herein by reference). A reactor may contain one or more parallel elongate hollow bodies, in which the reaction is performed. The definitions of the term "hollow body" shall be used in order to describe all of the hollow bodies for the reaction, unless provided for other purposes, such as preheating. The reaction fluid is conveyed in the hollow bodies, this being controlled by the inlet of the starting material (or starting materials). The fluid is referred to as a reaction fluid as soon as all conditions necessary for oxidation are present (all substances for reaction are present, temperature, pressure).

The hollow body or hollow bodies of a suitable reactor can be scaled arbitrarily to the necessary dimensions. However, in the case of the exothermic oxidation of tertiary amines, the necessary temperature control, i.e. heat discharge, must be respected. To this end, a reactor in which a temperature-control fluid is flushed around the hollow body is best suited. A reactor of this kind is described in WO 2010/055034. It has been found that, in the case of the oxidation reaction according to the invention, specific dimensions are advantageous. In particular, the inner diameter of a hollow body of the reactor is preferably 0.25 mm to 10 mm, preferably 0.5 mm to 6 mm, particularly preferably 0.8 mm to 4 mm. the length of a hollow body of the reactor is preferably 0.5 m to 20 m, preferably 1 to 10 m, in particular 2 m to 5 m. Other geometries are also possible. In the case of thicker hollow bodies a larger surface for increased temperature exchange may be necessary. The temperature exchange of the internally-guided reaction fluid may also be improved by feeding the reactants at a lower concentration, or by higher flow velocities of the reaction fluid, or via the externally guided temperature-control fluid by increasing the flow velocity, or the selection of a temperature-control fluid with higher heat capacity.

For oxidation of the tertiary amine, an oxidant can be fed. A group of oxidants is constituted for example by peroxides, wherein hydrogen peroxide is most preferred. Other peroxides are for example percarboxylic acids. Other oxidants, for example oxygen or ozone, can also be used. The tertiary amine is preferably used with a molar ratio to the oxidant of from 1:0.9 to 1:1.3, preferably from 1:1 to 1:1.1.

In particularly preferred embodiments the amine oxide is N-methylmorpholine N-oxide, which can be obtained by oxidation of N-methylmorpholine. The latter is therefore a preferred tertiary amine.

In accordance with the invention it has been found that the oxidation of the reaction fluid can be carried out well in a reactor such as a milli- or micro-structured apparatus with a surface-to-volume ratio of 0.5 $m^2/m^3$ or more—at least over a length of the hollow body in which the tertiary amine is oxidised to an extent of 50% (mol %) (first region, as explained above). The surface can be determined by the inner surface of the hollow body. The surface-to-volume ratio is calculated mathematically by dividing the surface area ($m^2$) by the volume ($m^3$), as evident from the specification "$m^2/m^3$". The dimension in the interior of the hollow body (reaction tube) is hereby described. Further background literature regarding this variable can be found in Némethné et al. (Materials Science and Engineering 39(2), 2014: 89-101). Higher surface-to-volume ratios, for example of 1 $m^2/m^3$ or more, 1.5 $m^2/m^3$ or more, or 2 $m^2/m^3$ or more are particularly preferred. With these dimensions the process parameters such as flow velocity and temperature in the oxidation of tertiary amines can be controlled very efficiently in a continuous process. As a result of this high surface-to-volume ratio compared to batch methods, large volume-based heat flows (cooling and heating of the reactants and of the reaction fluid) and intense mixing are made possible. This intense mixing in turn ensures that the reaction is performed very specifically and completely. The region "over a length of the hollow body in which the amine is oxidised to an extent of 50% (mol %)" in the method according to the invention relates to the region of the hollow body in which at least half of the amine is oxidised. This can be controlled easily by a person skilled in the art by selection of the flow velocity and concentration of the used reacting substances (tertiary amine, optionally oxidant such as peroxide).

A further parameter for characterising the method according to the invention is the specific surface load, which should be in the range from 1 l/m²h to 40 l/m²h, preferably from 5 l/m²h to 30 l/m²h or from 10 l/m²h to 20 l/m²h. The specific volume load is an alternative or further characteristic value of the method according to the invention, and should be from 1000 l/m³h to 30000 l/m³h preferably from 1500 l/m³h to 25000 l/m³h, particularly preferably from 2000 l/m³h to 20000 l/m³h. These specific loads, depending on the volume in the hollow body or inner surface of the hollow body, indicate the dimensioning of the reactor or of the fluid transported therein relative to the reactor surface, by which the reaction conditions in the reaction fluid can be controlled. The "specific surface load" (l/m²h) and "specific volume load" (l/m³h) are known terms which are additionally clear by the specification of the units. The term of surface load (also volume-to-surface load or volume surface loading) is used in the publication by Hoffmann et al. (Combination of Anaerobic Treatment and Nutrient removal of Wastewater in Brazil, 2010) and in Hessel et al. (Micro Process Engineering, comprehensive Handbook, Wiley-VCH, 2009) referred to in the latter as mass-to-surface load (kg/m²s). Further background literature regarding the variable of volume load can be found in Margesin et al. (publisher), Praxis der biotechnologischen Abluftreinigung (Biotechnological Waste Air Treatment Practices), Springer 1996, page 29). These variables specify the throughput of the reaction fluid (here in $1=10^{-3}$ m³) through the hollow body by volume (in m³) or by surface area of the hollow body (in m²) and by time (here in h).

These parameters (specific surface load and specific volume load and also surface-to-volume ratio) are selected such that, even with laminar flow, an efficient conversion and reaction is achieved in accordance with the invention in the hollow body—in particular in a milli- or micro-structured tube reactor for continuous operation. Of course, these parameters can be combined, for example all 3 or the surface-to-volume ratio (as dimensional variable of the hollow body) with the specific surface load or the specific volume load, preferably with the specific surface load.

An efficient reaction in a tube reactor with small diameter or with the specified surface-to-volume ratios is not easily optimised. On the one hand, small tube diameters (capillaries) have the advantage of an efficient reaction (yield and speed on account of high surface). On the other hand, the small tube or capillary diameters limit the fluid throughput in conjunction with the fluid-generated pressure losses occurring in the capillaries. In conclusion, a reaction that progresses surprisingly well was surprisingly determined with the parameters according to the invention under consideration of these advantages and disadvantages.

The reaction fluid is usually converted in the reactor with a laminar flow. The reaction fluid is preferably guided with a laminar flow in the hollow body. A laminar flow is to be distinguished from a turbulent flow. A turbulent flow is a movement of fluids where turbulences occur to a widely varying extent. Here, high friction and pressure losses occur, which lead to a higher heat development, in particular in the milli- or micro-structured reactor according to the invention. By contrast, in the case of a laminar flow there is no turbulence. Turbulent and laminar flow can be controlled by viscosity of the moved fluid, tube dimension (characteristic length, cross-sectional diameter), and the selected flow velocity. A measure for this is the Reynolds number, which is—as known in the literature—defined as $Re=\rho v d/\eta$ or $Re=vd/\nu$, wherein $\rho$ is the density of the fluid, v is the flow velocity of the fluid, d is the characteristic length of the hollow body (diameter, width or height), $\eta$ is the dynamic viscosity, and $\nu$ is the kinematic viscosity. A Reynolds number of 2300-2500 is usually the transition region between laminar and turbulent flow, wherein laminar flows are found at lower Reynolds numbers. Thus, the reaction fluid in accordance with the invention is preferably guided in a flow through the hollow body at a Reynolds number of 2300 or less, preferably at a Reynolds number of 2000 or less, particularly preferably at a Reynolds number of 1500 to 1, or 1200 to 10. In the following examples Reynolds numbers even in the range of 2-30 or 3-11 are provided, which are likewise preferred. Further possible Reynolds numbers are 800 or less, 500 or less, 300 or less, for example in combination with the aforementioned lower values.

Example values for calculating the Reynolds number are known material variables. For example, NMM from Alfa Aesar (catalogue no. A12158) can be used, which according to the product datasheet, has a dynamic viscosity n at 20° C. with 0.91 mPas. The density $\rho$, with 0.92 g/cm³, is >920 kg/m³ at 20° C. With a capillary diameter in the hollow reactor of for example 1 mm and a fluid speed of from 0.21 to 0.62 m/min, a Reynolds number of from 3 to 10 is given. All of these parameters are preferred variables of the fluids, hollow body and process parameters according to the invention, independently of the manufacturer and the exemplary substances.

The reaction fluid preferably has a dynamic viscosity of from 0.1 mPas to 10 mPas at 20° C. or under reaction conditions. The reaction fluid preferably has a density of from 0.1 g/cm³ to 2 g/cm³ at 20° C. or at reaction temperature.

Since the oxidation of tertiary amine to amine oxide is subject to a great heat of reaction, in the case of NMM to NMMO with an adiabatic temperature rise up to 400 K and a specific reaction enthalpy of up to −1600 kJ/kg, this can be made possible in a particularly effective manner with the method presented in accordance with the invention. The handling of such extremely exothermic reactions, such as the oxidation of NMM to NMMNO, requires extremely high volume-specific and throughput-specific heat flows. This means, in the method according to the invention, that overheating at specific points (hot spots), which can occur very easily and in an uncontrolled manner in batch reactors, are avoided. The intense energy dissipation of the method according to the invention makes it possible for the speed of the oxidation from tertiary amine into amine oxide to be raised with corresponding temperature and pressure adaptation, without occurrence in the tube reactor of significant temperature differences prevailing in different areas, which, under extreme consideration, could signify the "thermal runaway" of the reaction and would additionally have an adverse effect on the selectivity of the reaction. With the method presented in accordance with the invention it has been found that amine oxide can be produced under more controlled process temperatures and higher pressures compared to the prior art.

In the second region, i.e. a region after which already 50% (mol %) of the tertiary amine has been oxidised, lower surface-to-volume ratios can be selected, wherein values overlapping with the first range are also possible. In the second region the surface-to-volume ratio is preferably 5 m²/m³ or less, particularly preferably 4 m²/m³ or less, 3 m²/m³ or less, or 2 m²/m³ or less.

Of course, other region divisions with different temperature conditions, in particular a different temperature control, that is to say a different heat transport (away) from the reaction fluid, are also possible. Such region divisions based on the progression of the oxidation of the tertiary amine, i.e. for example a region division into parts of the reaction fluid up to reaction progression limits at which 25%, 33% or 50% of the tertiary amine has been oxidised.

With a suitably dimensioned hollow body, various parameters can be adjusted on the basis of the flow rate (or flow velocity) of the reaction fluid (with the starting material), for example the residence time of the tertiary amine in the reactor. The residence time is preferably from 0.4 minutes to 14 minutes, preferably 0.6 to 8 minutes. The reaction progression in $$X_A = \frac{\tau c_{A,0} k}{1 + \tau c_{A,0} k}$$

individual regions can also be controlled by means of the residence time. The relationship of the residence time and the oxidation behaves approximately similarly to a second-order chemical reaction. The conversion and the residence time of a second-order reaction are related via the following formula:

k ... speed constant of the chemical reaction in $lmol^{-1}s^{-1}$
$c_{A,0}$ ... starting concentration of the reactant A (tertiary amine) in $moll^{-1}$
τ ... residence time in s
$X_A$ ... conversion of the reactant A (tertiary amine) as a proportion This kind of residence times in relation to conversions are shown for the case of NMM in FIG. 1. As discussed, residence times can be adjusted via the flow velocity. The flow velocity also influences the temperature control and the division of the reactor into corresponding regions, since, as the reaction progresses, tertiary amine is consumed, its concentration therefore decreases, and consequently the reaction also slows, whereby thereafter less heat is released. A preferred flow velocity of the reaction fluid, which is suitable for all factors, is 0.1 m/min to 60 m/min, preferably 10 m/min to 40 m/min, most preferably 20 m/min to 25 m/min. Further preferred flow velocities of the reaction fluid, which is also suitable for all factors, is 0.1 m/min to 200 m/min, preferably 10 m/min to 160 m/min, most preferably 10 m/min to 120 m/min.

It is also possible to choose different flow velocities in different regions (in particular as defined above, depending on the progress of the reaction). Different flow velocities are given with different hollow body cross-sections in the different regions.

In addition to the control, a different reaction speed in individual regions can thus be controlled alternatively or in combination.

The specific reaction heat is preferably between 540 kJ/kg and 1610 kJ/kg, preferably between 1110 kJ/kg and 1420 kJ/kg. This value is maintained particularly preferably in the first region (reaction up to 50% of the tertiary amine, as defined above).

Quicker reaction speeds can be achieved in the amine oxide production by increasing the process temperature. However, on account of the strong exothermic nature of the chemical conversion of tertiary amine (such as NMM) into the formed amine oxide (such as NMMNO), there is a risk of self-acceleration, accompanied by an uncontrolled rise in temperature and pressure. Incidentally, the product quality in an uncontrolled higher temperature range is negatively influenced. The selectivity of the conversion reaction decreases, and undesirable by-products may be formed. Such by-products may be based on tertiary N-methylmorpholine (NMM), for example morpholine (M) and nitrosomorpholine (NMOR). For these reasons, the reaction temperature in the hollow body or the reaction fluid is preferably 20° C. to 70° C., preferably 50° C. to 65° C., most preferably from 55° C. to 65° C., for example 60° C. to 65° C. This temperature can be adjusted by a corresponding temperature-controlled jacketing of the hollow body of the reactor.

A preferred pressure in the hollow body is 1 bar to 200 bar, preferably 5 bar to 100 bar, most preferably 50 bar to 100 bar. Pressures or pressure ranges for the reaction according to the invention are preferably (all in bar) 1, 10, 20, 30, 40, 50, 60, 70, 80, 90, 100, 110, 120, 140, 160, 180, 200 or values between these pressures. A quick reaction takes place at these pressures. Furthermore, $CO_2$ can better dissolve and thus better mix with the product fluid at high pressures.

The hollow bodies can consist of various materials, for example metals, ceramics or plastics. The inner wall of the hollow body may influence the oxidation reaction. The inner wall of a hollow body of the reactor preferably contains one or more metals, preferably selected from Fe, Cr, Ni, Mo, Mn, Nb, Au, Pt, Ti or mixtures hereof. High-grade steels of classes 1.43, 1.44 and 1.45 are particularly suitable, since these have a very high thermal conductivity alongside a good corrosion resistance with respect to heavily oxidative media (for example $H_2O_2$). An inner wall of a hollow body preferably contains austenitic steel. In addition, the hollow body material should be pressure-resistant—depending on the desired reaction pressure. This combination of high thermal conductivity, high corrosion resistance and high pressure resistance requires usually metal or ceramic materials. Plastics can be used for fittings (for example static mixers) or additional coatings. As inlays or fittings, which are used above all for the purpose of improved mixing of the reaction solution, merely a high resistance to corrosion is required, wherein here materials such as those mentioned above, but in particular also iron, titanium, gold, platinum, ceramic, glass, PTFE, PEEK, etc., are used.

Figure 7:
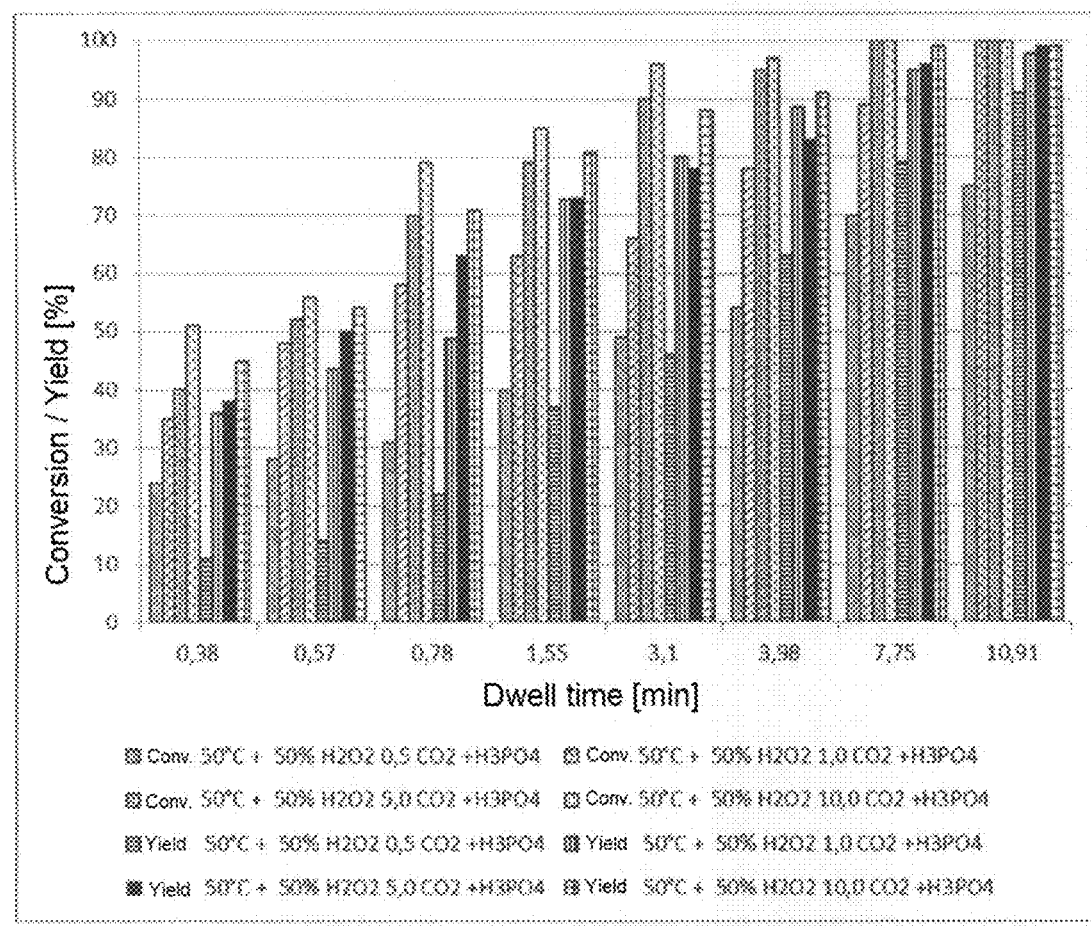
FIG. 7 shows the influence of the $CO_2$ concentration on the reaction speed.
Figure 8:
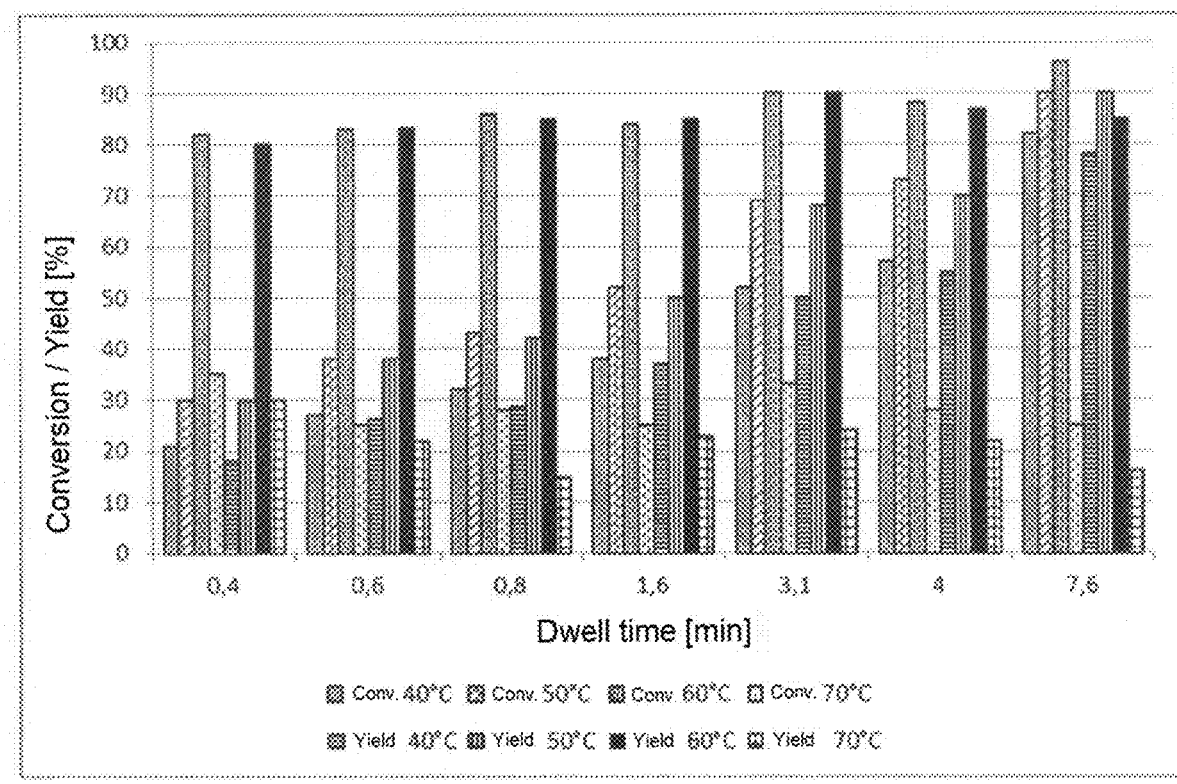
FIG. 8 shows the influence of the temperature on the reaction progress, conversion-yield curve with 30% by weight $H_2O_2$, 1% by weight $CO_2$, and 0.1% by weight $H_2PO_4$.

The hollow bodies can assume any arbitrary form, for example the inner cross-section can be round, circular, square, semi-circular, hexagonal, octagonal, etc. The hollow bodies are preferably tubes, also preferably with a round, circular, square, semi-circular, hexagonal, octagonal, etc. inner cross-section. The reactor according to the invention is also referred to herein as a tube reactor. In addition, fittings are possible which are provided at arbitrarily selected distances or also sporadically. Fittings of this kind are for example constrictions or pinch points for increasing the turbulence of the flow, in particular for improved mixing of the fluid in the tube. Also, one or more static mixers (for example mixing plates) or perforated plates can be provided. Mixing times of from 1 ms to 1 s are preferred. Suitable perforated plates for mixing are shown for example in FIG. 14 of WO 2010/055034 (incorporated herein by reference). Suitable pinch points are shown in FIGS. 7 and 8 of WO 2010/055034.

The tertiary amine can be fed into the reactor in a concentration of 40% to 100%, preferably from 50% to 99.5%, in particular 60% to 99%, especially preferably 70% to 99%, also 60% to 98% or 70% to 97% (all % in vol. %). These concentrations can also be present at the start of the reaction, optionally diluted depending on the volume of an added fluid with oxidant or other additives.

An oxidant, in particular hydrogen peroxide, is preferably fed into the hollow body in a concentration of from 5% to 80%, preferably from 10% to 70%, in particular 20% to 60%, especially preferably 30% to 55% (all % in % by weight). The amount should be coordinated with the tertiary amine so that the above ratios, in particular 1:1 mol equivalent tertiary amine to oxidant, in particular peroxide, are satisfied.

The reaction fluid can be conveyed through the reactor at a Bodenstein number of greater than 10, preferably from 20 to 200, according to the formula $$Bo=u*L/D_{ax},$$

in which Bo is the Bodenstein number, u is the flow velocity of the reaction fluid, L is the length of the hollow body of the reactor, and $D_{ax}$ is the axial dispersion flow of the reaction fluid. To this end, a suitable flow velocity with given reactor/hollow body geometry can be selected. The Bodenstein number describes the degree of backmixing in the reactor. It is the ratio between the convection flow (u*L) and the axial dispersion flow. Suitable mixing states for the introduction of the amine and the oxidant in order to form the reaction fluid and for the further course of the oxidation are provided in the region of the selected Bodenstein numbers.

Preferably, $CO_2$ is introduced into the reaction fluid in an amount of 0.5% by weight to 20% by weight, in relation to the tertiary amine. $CO_2$ can be introduced into the microreactor together with the amine or the oxidant or separately, preferably following prior saturation in solution or at least at 90% of the saturation concentration in the solution in question, or can be fed directly into the microreactor. The solution of $CO_2$ is preferably basic, for example with a pH 8-11 or 9-10, in order to increase the solubility of $CO_2$. $CO_2$ is preferably in the tertiary amine, optionally dissolved with water, or directly introduced into the reaction fluid, for example fluid under pressure or as a solution in water. $CO_2$ can significantly accelerate the oxidation of tertiary amines into amine oxide, specifically by 460 times in the case pf NMM to NMMO. Mechanistically there is a reaction of peroxide ($RHO_2$, in particular $H_2O_2$) with $CO_2$, and the formed peroxymonocarbonate $HCO_4^-$ or also $RCO_4^-$ acts in an accelerating manner on the reaction from NMM to NMMO, that is to say is itself a more active oxidant in comparison to the used oxide form (such as $H_2O_2$). Since $CO_2$ thus can be used itself as reaction partner, a high concentration may positively influence the reaction. In tests with the reactor according to the invention it was found that particularly high and effective $CO_2$ amounts (for example if completely dissolved or almost completely dissolved) can be used. $CO_2$ is preferably fed under pressure and in dissolved form to the reaction fluid. The above-mentioned $CO_2$ amounts of dissolved $CO_2$ are preferred. In the continuous system according to the invention particularly high $CO_2$ amounts can be achieved, and these have positive effects on the reaction. For example, the $CO_2$ amount may be at least 0.5%, at least 1%, at least 2%, at least 4%, at least 6%, at least 8%, at least 10%, or at least 15%, all % by weight, in relation to the tertiary amine or another solution of $CO_2$ introduced into the reaction fluid. These amounts are likewise possible in relation to the total reaction fluid.

In addition, a metal complexing agent, preferably a phosphate, can be added to the reaction fluid, preferably in an amount of from 0.01% to 3%, preferably 0.03% to 2%, especially preferably 0.05% to 1.5% (all % by weight). Undesirable metals in the fluid may break down the oxidant and therefore reduce the reactivity with respect to the tertiary amine. The metal complexing agent is therefore intended to prevent or reduce this effect of the metal. Any complexing agent, for example a chelating agent is possible (as mentioned for example in the introduction). It has surprisingly been found that phosphate is likewise suitable, in particular in the case of iron-containing reactor materials, which can release iron or the iron casing of which may have an interfering effect at the surface relative to the reaction fluid. This could be reduced by means of metal complexing agents, such that approximately 10% higher yields can be attained.

The tertiary amine oxide is preferably preheated before it is oxidised. The preheating is performed in particular to the temperature desired in the reaction fluid, for example selected from the above-mentioned temperatures. Preheating can be performed in a reactor or hollow body, as described above, and can be performed relatively quickly at appropriately high surface-to-volume ratios (for example ratios similar to those during the above-presented reaction). Preheating can be performed for example within a period of time from 5 sec to 5 min, preferably approximately 1 min. "Approximately" means+/−20%.

The oxidant may also be preheated. To this end, the measures and parameters described for the tertiary amine may also be selected, for example preheating within a period of time from 5 sec to 5 min, preferably approximately 1 min.

Following the desired reaction progress, for example when the entire tertiary amine or almost the entire tertiary amine (for example 99.5 percent or more) has been oxidised, any remaining oxidant can be broken down or removed. In the case of peroxides, in particular hydrogen peroxide, the use of catalase or treatment with another catalyst, such as $MnO_2$ or platinum (for example platinised nickel) is suitable. The catalyst can be used in the form of bundles or particles inherently of high surface (for example Katapak®) or as a catalyst plate.

Instead of clean tertiary amines, concentrated vapours, which are produced during the production of cellulose fibres, can also be used. The concentration is performed as described in EP 0 448 924 by reverse osmosis. Morpholine is distilled off in a subsequent step as described in EP 0 448 924 and can likewise be oxidised following a methylation, as described for example in patent DE 3504899 A1.

The amine oxide produced in accordance with the invention, preferably NMMO, can be used directly. The continuous method according to the invention is suitable here for use of the continuously produced amine oxide in a downstream plant, likewise operated continuously. A coupled downstream process of this kind is for example the dissolution of cellulose in NMMO or other amine oxides. As mentioned in the introduction, a cellulose solution in amine oxide can be used for a spinning method (lyocell method). Here, filaments, fibres or films can be formed and produced from the cellulose solution. This can also be combined in-line or off-line with the method according to the invention, similarly to the dissolution process.

As appropriate, the amine oxide produced in accordance with the invention can be concentrated or diluted, preferably following breakdown or removal of the oxidant. The concentration of the obtained amine oxide is preferably set to 20%-60%, particularly preferably to 30%-50% (all % by weight). Compositions of this kind are well suited for storage or transport (including transport through pipelines in a coupled plant). Higher concentrations are preferably set for the dissolution of cellulose. The produced amine oxide may thus be set to a concentration of from 50% to 95%, preferably 60% to 90% or 70% to 80% (all % by weight). Water or any other permissible liquid can be used as diluent.

When dissolving and/or for spinning cellulose in the produced amine oxide, a solution with 4% to 30%, preferably 8% to 25% or 10% to 20% cellulose is preferably produced (all % by weight). A suitable spinning solution for example has the following composition: cellulose 12.9%, NMMO 76.3%, water 10.8%, all % by weight, (see WO 2013/030400, incorporated herein by reference). WO 2013/

030400 also describes a spinning method which can be used in accordance with the invention. Generally, the cellulose solution can be extruded with the amine oxide produced in accordance with the invention, wherein the extrudates pass through a gas gap and are introduced into a precipitation bath. The precipitation bath may comprise a precipitant, for example water, in a concentration for precipitation of the cellulose. A gas flow can be guided in the gas gap, as commonly known.

Accordingly, the present invention also comprises a method in which the amine oxide produced in accordance with the invention is brought to a concentration for dissolving cellulose and furthermore optionally the cellulose is dissolved therein and furthermore optionally the dissolved cellulose is shaped into continuous shaped bodies, for example filaments, threads or films, for example by extrusion, and then the cellulose of the shaped bodies is precipitated.

Figure 2:
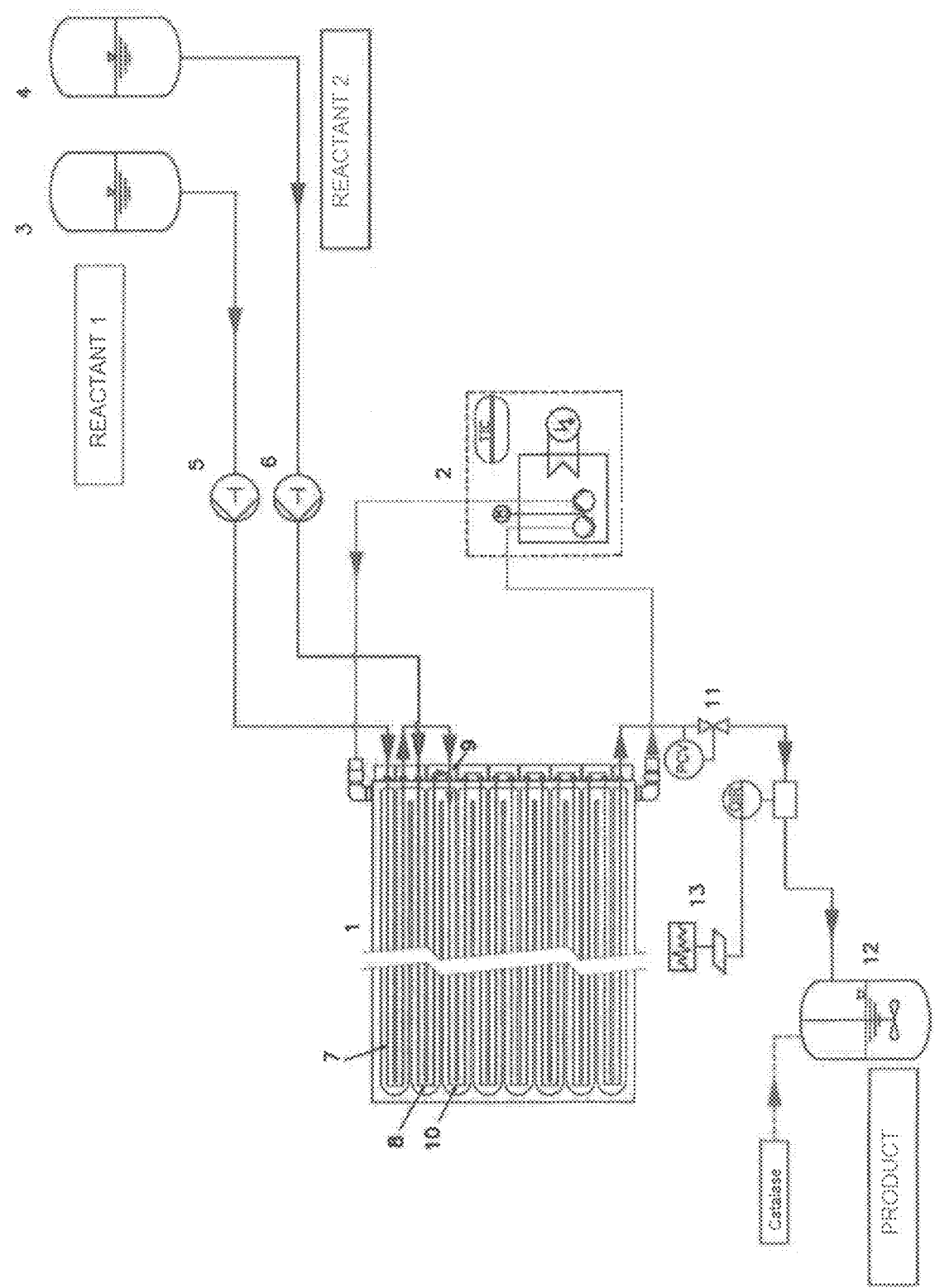
FIG. 2 shows a microreactor (1) with feed of the reactants (3, 4) via the pumps (5, 6) and discharge after the pressure-sustaining valve (11) to the product container (12).
Figure 11:
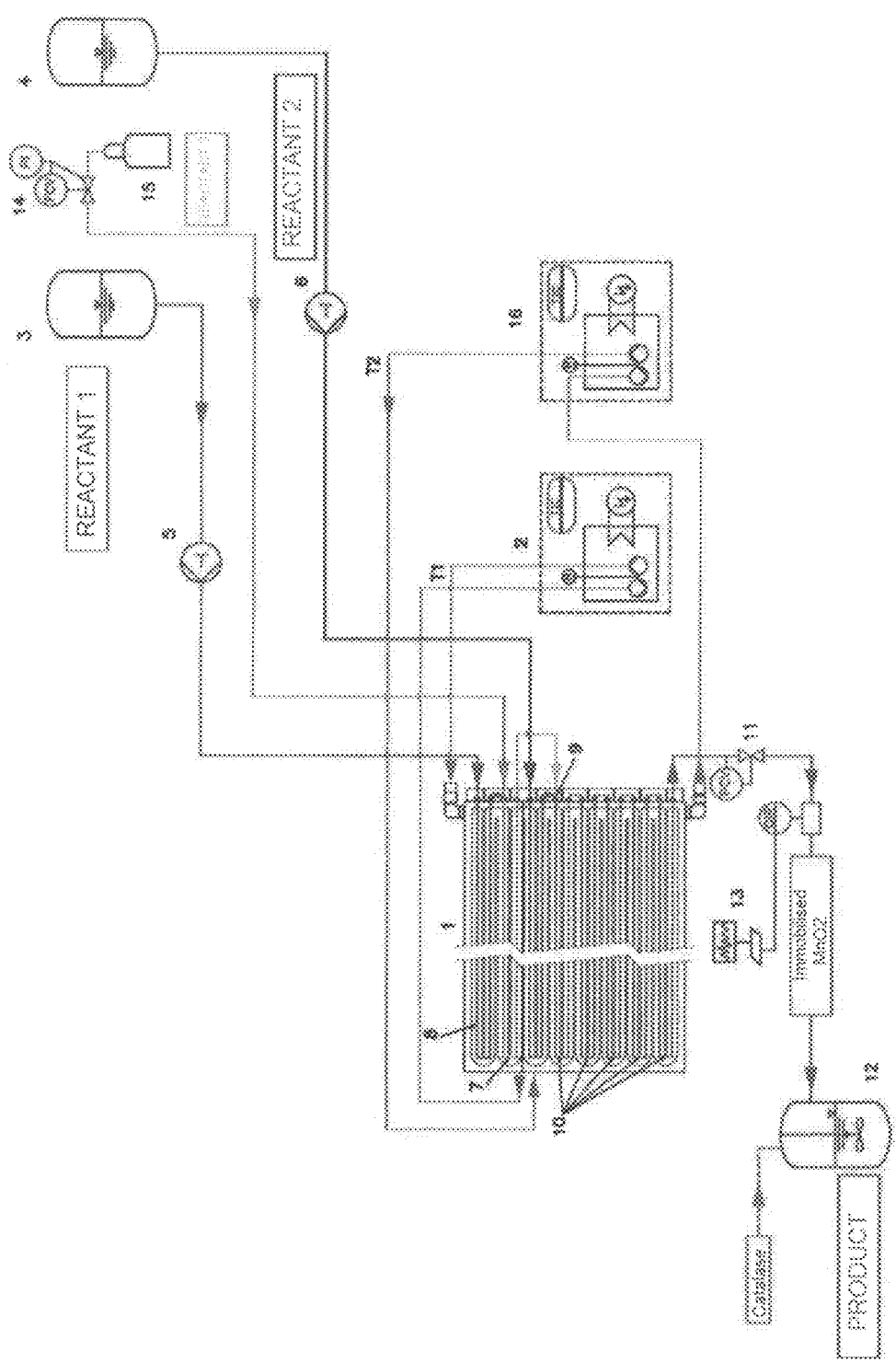
FIG. 11 shows a microreactor similar to FIG. 2 with additional feed for a third reactant (for example $CO_2$).

Reactor System:

A reactor according to the invention in a reactor system is shown in FIGS. 2 and 11. A microreactor (1) as described in WO 2010/055034 was used. The reactor system has a tube reactor (1), which is used to guide the reaction fluid and to preheat the two reactants (tertiary amine and oxidant). The reactants are guided from storage containers (3, 4) via pumps (5, 6) to the reactor (1). There, the reactants are preheated in zones 7 and 8. A temperature-control medium is guided around the hollow bodies for heating. The temperature-control medium is heated or cooled in the thermostat (2). The preheated reactants are combined at the position 9, whereby the reaction fluid is produced and is guided through the hollow bodies, for example reactor tubes 10. Pressure is controlled both via the pumps (5, 6) and via a pressure-sustaining valve (11). The product is collected in a container (12), which has an agitator. Here, further reactions can be performed optionally, for example complete oxidation of remaining amine or breakdown of oxidant(s). A measuring apparatus with flow-through cell (13) can optionally monitor the product discharge.

The present invention will be further explained and described in greater detail by the following examples, without being limited to these embodiments of the invention. All parameters and apparatus parts of these examples can also be combined with the above-mentioned primary aspects of the invention or the preferred embodiments independently of the rest of the description of the examples.

EXAMPLES

Chemicals:

The chemicals used to perform the experiments were procured in different purities from various suppliers. Table 1 shows a list of the chemicals used to carry out the tests.

TABLE 1

| | | Chemicals | | |
|---|---|---|---|---|
| Name | Supplier | Purity [%] | Catalogue number | CAS number |
| NMM | Alfa-Aesar | ≥99 | A12158 | 109-02-4 |
| $H_2O_2$ 30% | Sigma | — | 216763 | 7722-84-1 |
| $H_2O_2$ 50% | Sigma | — | 516813 | 7722-84-1 |
| Catalase (store at −20° C.) | Sigma | 2,000-5,000 units/mg | C-9322 | 9001-05-2 |

TABLE 1-continued

| | | Chemicals | | |
|---|---|---|---|---|
| Name | Supplier | Purity [%] | Catalogue number | CAS number |
| $CO_2$ N45 | Air Liquide | 99.995% | | |
| Potassium permanganate | Sigma | 0.2M | 35184 | 7722-84-1 |
| Phosphoric acid | Carl Roth | 75%, ultrapure | 2614.1 | 7664-38-2 |
| Sulfuric acid | Bernd Kraft | 2.5M | 03279.3000 | |
| Coolant water/ethylene glycol 1/1 vol./vol. HPLC-UV | | | | |
| Morpholine | Sigma | ≥99 | 252360 | 110-91-8 |
| NMMNO $xH_2O$ | Alfa-Aesar | 98+ | A15996 | 70187-32-5 |
| NMMNO 50% by weight in $H_2O$ | Alfa-Aesar | | A19802 | 7529-22-8 |

Reaction System According to FIG. 2

Dissolution of $CO_2$ in N-Methylmorpholine

In order to increase the reaction speed, reactant 1 is saturated with [F] % by weight of $CO_2$. This was achieved for example by introducing $CO_2$ into the NMM solution via a gas introduction tube or a sintered, porous device. NMM was also exposed to a $CO_2$ atmosphere in order to dissolve $CO_2$ in NMM under stirring at 0.1-20 bar overpressure. Once the dosing was complete, the reactant solution enriched with $CO_2$ was weighed for checking purposes and was used for the microreactor tests.

Execution of the Reaction in the Microreactor

The microreaction system used by us is based on WO 2010/055034 and was produced from the material [A] according to the table. The microreactor tests for the synthesis of N-methylmorpholine N-oxide (NMMNO) from 4-N-methylmorpholine (NMM) and hydrogen peroxide ($H_2O_2$) were carried out in different fittings in the microreactor. The characteristic data of the used reactor (1) are as follows:

volume: variable, up to 26 mL
capillary diameter: 1 mm, tubes with pinch points

Since the reaction of NMM with $H_2O_2$ to form NMMNO is exothermic (adiabatic temperature increase 335 K), it must be ensured in the case of this reaction that the microreactor conditions and technical design are selected such that the conditions are sufficiently suitable for the heat transport, such that on the one hand heat can be fed to the reaction system to the reactant NMM, and on the other hand heat can be removed from the reaction solution. This is achieved by sufficiently dimensioned microreactor surfaces. Thanks to the large exchange area between reaction medium and temperature-control medium, the heat can be discharged in a controlled manner, and there is no need for long dosing times, which in batch methods last for several hours. Furthermore, smaller reaction volumes are found in the microreactor, whereby the safety of the method is significantly increased. Due to the improved process control, and improved quality, selectivity and a higher yield can be provided. Furthermore, the test setup makes it possible to work under increased pressure, whereby the material transport/phase transfer improves significantly compared to a batch reactor.

An ECO SILVER RE415 heating thermostat (2) from the company Lauda was used in order to control the temperature of the microreactor to [B] ° C. A mixture of water/ethylene glycol in a ratio by volume of 1:1 was used as cooling and heating medium.

The two reactants were stored in two storage containers (3, 4)

TABLE 2

| Reactants | | |
|---|---|---|
| | Reactant 1 | Reactant 2 |
| Volume flow | [C] ml/min | [D] ml/min |
| Molar ratio | | [E] |
| Composition | 8.5M N-methylmorpholine presaturated with [F] % by weight $CO_2$ | [G] % by weight hydrogen peroxide with [H] dissolved $CO_2$ and [I] % by weight $H_3PO_4$ |

The volume flow rates of the chemicals were controlled via two computer-controlled pumps (5 and 6) of the SyrDos and HiTec Zang type and were combined after the preheating tubes (7 NA) via a mixing module T3 with inserted static mixer (for example mixing plate) (9), according to WO 2010/055034. Different mixing inserts can be used in the mixing module. The reaction mixture is then guided into the reaction tubes (10), where the reaction takes place. In order to increase and regulate the pressure in the reactor, a pressure-sustaining valve (11) for the range 0-20 bar was used before the flow-through cell and was controlled to [J] bar. A further pressure-sustaining valve can be installed after the flow-through cell in order to avoid a formation of gas in the cell. The incorporation of the pressure-sustaining valve is intended to suppress the decomposition reactions and secondary reactions to the greatest possible extent, since there may be a development of gas during the course of these undesirable reactions.

The desired product was collected in a vessel comprising an agitator (12). Excess hydrogen peroxide was broken down by slowly adding drops of 0.5% by weight catalase solution and then subjecting the mixture to a peroxide test.

Throughputs of [K] ml/min with conversions of [L] % and yields of [M] % could be achieved.

TABLE 3

| Method parameters | |
|---|---|
| Fluid speed | [N] m/min |
| Hydrodynamic residence time in the reaction region | [O] min |
| Reactor-specific surface load | [P] l/m²h |
| Reactor = specific volume load | [Q] l/m³h |
| Surface:volume ratio | [R] |

Analytics

The quality of the product was recorded via an online FT-IR measurement (13) in a flow-through cell using an Alpha spectrometer from BRUKER. The peak at 1045-1028 cm$^{-1}$ which can be associated with the reactant was used to monitor the conversion. The peaks that can be associated with the NMMNO appear at the wave numbers 1250-1215 cm-1, 995-960 cm$^{-1}$ and 960-920 cm$^{-1}$. The peak at 1250-1215 cm$^{-1}$ was used in order to evaluate the yield.

The reaction samples were likewise analysed off-line by means of HPLC/UV. The samples were separated by means of liquid chromatography and were measured via a UV detector. The tests were assessed on the basis of the obtained chromatograms. An HPLC 1100 from the company Agilent Technologies was used for the analysis.

The obtained chromatograms from the calibration showed NMMNO at a retention time of 1.940 minutes, and NMM with a retention time of 17.341 minutes, and morpholine with a retention time of 5.461 minutes. The chromatograms of the injection of a synthetic produced reference mixture (NMM, NMMNO, M) showed that the substances are separated and can be determined from one another cleanly.

In order to determine any formed N-nitrosomorpholine (NMOR), on account of the concentrations of <100 ppb that are to be achieved, a gas chromatogram with mass spectrometry coupling was used, since in these ranges the accuracy of HPLC/UV systems is insufficient. NMOR can be extracted from the product by use of medium polar solvents. The use of a 1:1 mixture of dichloromethane (DCM) and ethyl formate (EF) has proven to be expedient in the sample preparation.

The product was likewise determined by way of refractometry at refractive indices of 1.330-1.449. The concentration of the synthesised NMMNO can be read off on the basis of the refractive index. The concentration of the product was also determined, via the density.

$CO_2$ Addition

Figure 3:
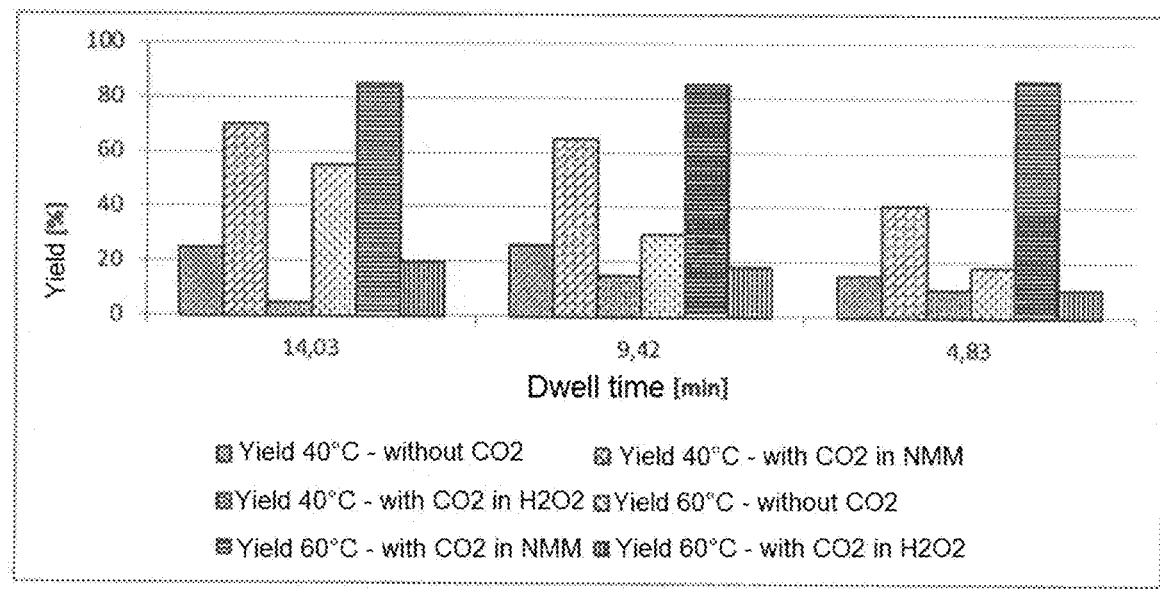
FIG. 3 shows the yield curve with different $CO_2$ addition.
Figure 4:
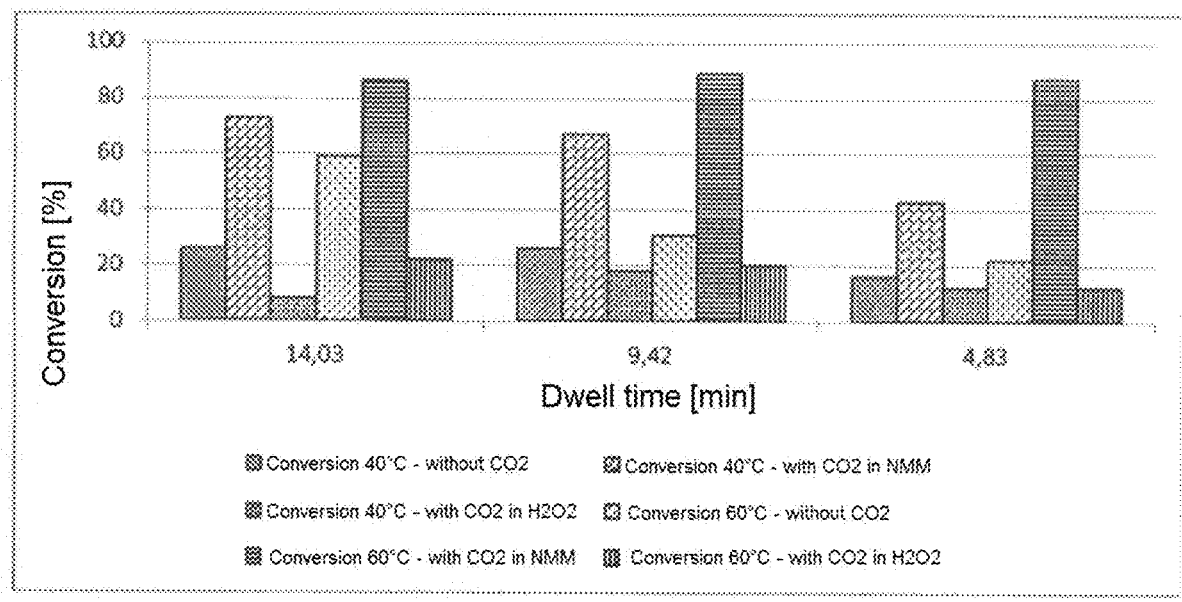
FIG. 4 shows the conversion curve with different $CO_2$ addition.

Tests were performed which were intended to show why the $CO_2$ should be dissolved for the greatest possible conversions and yields. It was found that the addition of $CO_2$ to the NMM had a positive effect on the yield in all cases (+40-70%, FIGS. 3 and 4). The reason for this lies in the high solubility of $CO_2$ in N-methylmorpholine.

With shorter residence times an increased temperature had a greater effect on the yield than with longer residence times. The reaction thus progresses more quickly at elevated temperatures, which increases the production rate as a result of the possible shorter residence times.

Figure 6:
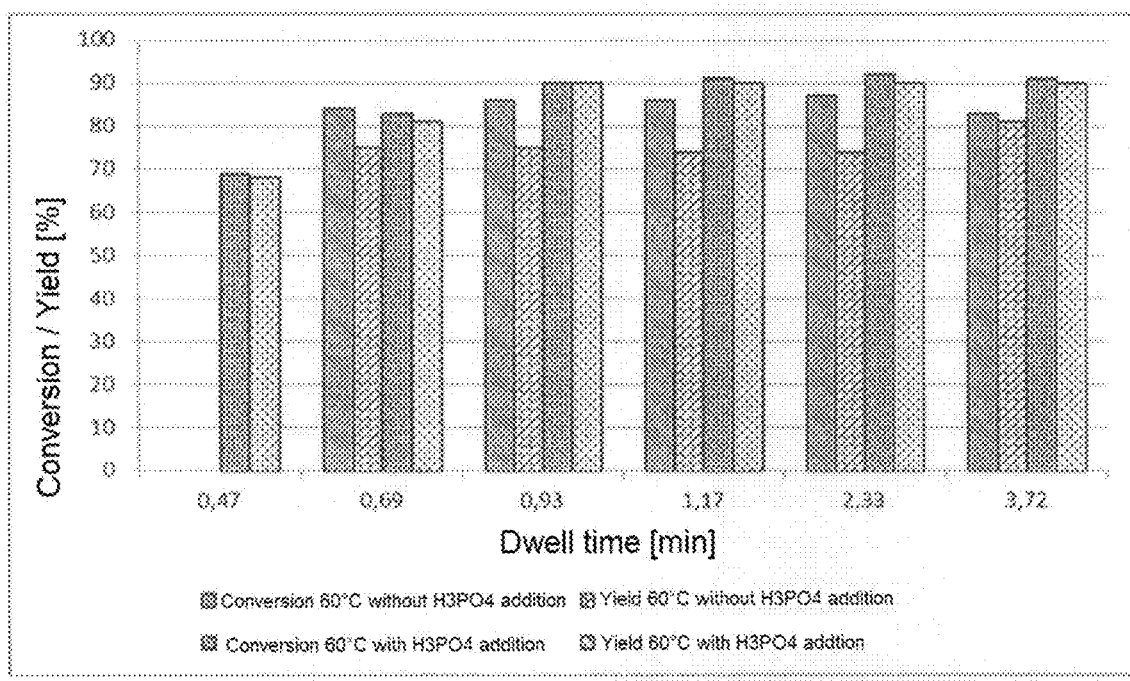
FIG. 6 shows the stabilisation of the hydrogen peroxide with phosphoric acid in order to improve the reaction.

Stabilisation of the Hydrogen Peroxide with Phosphoric Acid to Improve the Reaction Since hydrogen peroxide is always broken down at elevated temperatures, thus eradicating the reaction solution, it was attempted to suppress this by phosphoric acid. It could be found that the conversions and yields are increased by adding $H_3PO_4$ around 5-10% (FIG. 6). This effect intensifies with an increase of the residence time. Phosphoric acid acts as a complexing agent, which complexes catalytically acting metal ions, which could break down the hydrogen peroxide.

TABLE 4

| | | | | | | | | |
|---|---|---|---|---|---|---|---|---|
| | | C | D | E | F | G | H | I |
| | | Reactant 1 | Reactant 2 | Molar | $CO_2$ | | $CO_2$ | $H_3PO_4$ |
| | | N- | hydrogen | ratio | in | Concentration | in | in |
| | B | methylmorpholine | peroxide | reactant | NMM | $H_2O_2$ | $H_2O_2$ | $H_2O_2$ |
| A | Temperature | (NMM) | ($H_2O_2$) | 1:reactant 2 | [mass | [mass | [mass | [mass |
| Material | [° C.] | [ml/min] | [ml/min] | [mol/mol] | %] | %] | %] | %] |
| PTFE | 40 | 0.23 | 0.2 | 1:1 | 0 | 29 | 0 | 0 |
| | 40 | 0.34 | 0.3 | 1:1 | 0 | 29 | 0 | 0 |
| | 40 | 0.67 | 0.58 | 1:1 | 0 | 29 | 0 | 0 |
| | 40 | 0.23 | 0.2 | 1:1 | 0.5 | 29 | 0 | 0 |

TABLE 4-continued

Test parameters for CO₂ addition

| | | | | | | | |
|---|---|---|---|---|---|---|---|
| 40 | 0.34 | 0.3 | 1:1 | 0.5 | 29 | 0 | 0 |
| 40 | 0.67 | 0.58 | 1:1 | 0.5 | 29 | 0 | 0 |
| 40 | 0.23 | 0.2 | 1:1 | 0 | 29 | Fed | 0 |
| 40 | 0.34 | 0.3 | 1:1 | 0 | 29 | Fed | 0 |
| 40 | 0.67 | 0.58 | 1:1 | 0 | 29 | Fed | 0 |
| 60 | 0.23 | 0.2 | 1:1 | 0 | 29 | 0 | 0 |
| 60 | 0.34 | 0.3 | 1:1 | 0 | 29 | 0 | 0 |
| 60 | 0.67 | 0.58 | 1:1 | 0 | 29 | 0 | 0 |
| 60 | 0.23 | 0.2 | 1:1 | 0.5 | 29 | 0 | 0 |
| 60 | 0.34 | 0.3 | 1:1 | 0.5 | 29 | 0 | 0 |
| 60 | 0.67 | 0.58 | 1:1 | 0.5 | 29 | 0 | 0 |
| 60 | 0.23 | 0.2 | 1:1 | 0 | 29 | Fed | 0 |
| 60 | 0.34 | 0.3 | 1:1 | 0 | 29 | Fed | 0 |
| 60 | 0.58 | 0.58 | 1:1 | 0 | 29 | Fed | 0 |

| J Pressure [bar] | K Throughput [ml/min] | L Conversion [%] | M Yield NMMO [%] | N Fluid speed [m/min] | O Hydrodynamic residence time in the reaction region reactor length [min] | P Reactor-specific surface load [l/m²h] | Q Reactor-specific volume load [l/m³h] | R Surface:volume ratio |
|---|---|---|---|---|---|---|---|---|
| 6.89 | 0.43 | 26 | 25 | 0.21 | 14.03 | 1.71 | 4,277.42 | 2.5 |
| 6.89 | 0.64 | 26 | 26 | 9.42 | 9.42 | 2.55 | 6,366.39 | 2.5 |
| 6.89 | 1.25 | 16 | 15 | 4.83 | 4.83 | 4.97 | 12,434.35 | 2.5 |
| 6.89 | 0.43 | 73 | 70 | 14.03 | 14.03 | 1.71 | 4,277.42 | 2.5 |
| 6.89 | 0.64 | 67 | 65 | 9.42 | 9.42 | 2.55 | 6,366.39 | 2.5 |
| 6.89 | 1.25 | 43 | 41 | 4.83 | 4.83 | 4.97 | 12,434.35 | 2.5 |
| 6.89 | 0.43 | 8 | 5 | 14.03 | 14.03 | 1.71 | 4,277.42 | 2.5 |
| 6.89 | 0.64 | 18 | 15 | 9.42 | 9.42 | 2.55 | 6,366.39 | 2.5 |
| 6.89 | 1.25 | 12 | 10 | 4.83 | 4.83 | 4.97 | 12,434.35 | 2.5 |
| 6.89 | 0.43 | 59 | 55 | 14.03 | 14.03 | 1.71 | 4,277.42 | 2.5 |
| 6.89 | 0.64 | 31 | 30 | 9.42 | 9.42 | 2.55 | 6,366.39 | 2.5 |
| 6.89 | 1.25 | 22 | 18 | 4.83 | 4.83 | 4.97 | 12,434.35 | 2.5 |
| 6.89 | 0.43 | 86 | 85 | 14.03 | 14.03 | 1.71 | 4,277.42 | 2.5 |
| 6.89 | 0.64 | 89 | 85 | 9.42 | 9.42 | 2.55 | 6,366.39 | 2.5 |
| 6.89 | 1.25 | 87 | 86 | 4.83 | 4.83 | 4.97 | 12,434.35 | 2.5 |
| 6.89 | 0.43 | 22 | 20 | 14.03 | 14.03 | 1.71 | 4,277.42 | 2.5 |
| 6.89 | 0.64 | 20 | 18 | 9.42 | 9.42 | 2.55 | 6,366.39 | 2.5 |
| 6.89 | 1.25 | 12 | 10 | 4.83 | 4.83 | 4.97 | 12,434.35 | 2.5 |

Reactor Materials

The synthesis of NMMNO was carried out with different capillary materials. The highly corrosion-resistant material Hastelloy® C-22 was also tested. Hastelloy Alloys belong to the group of highly corrosion-resistant nickel-molybdenum alloys and are characterised by high contents of nickel, molybdenum and chromium. These materials are characterised by high resistances in reducing media.

Figure 5:
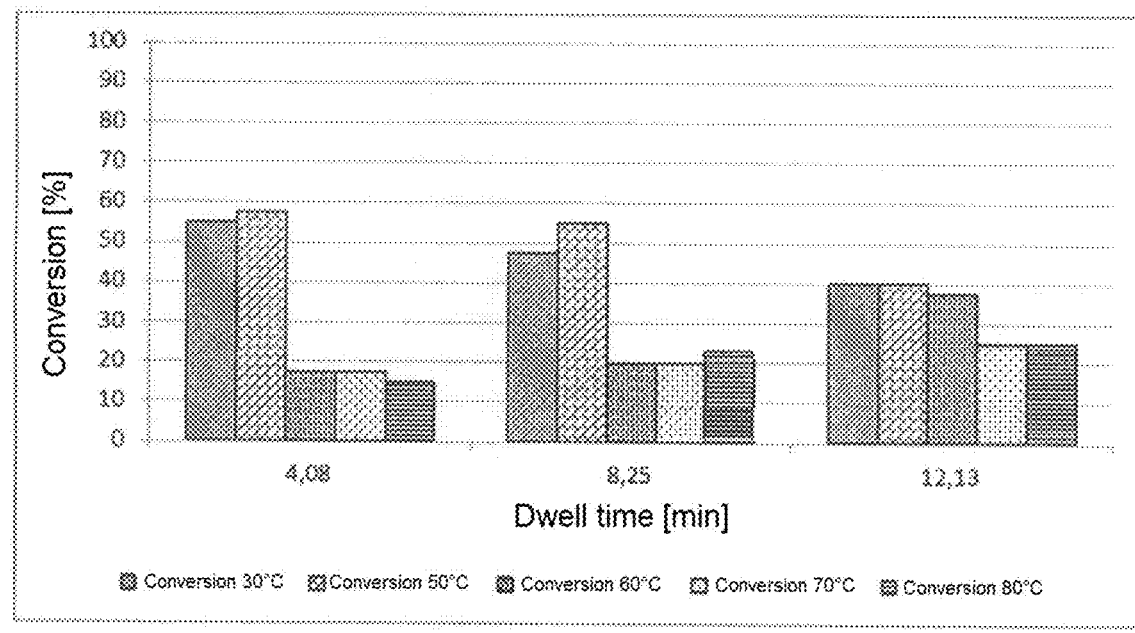
FIG. 5 shows conversions in a reactor made of Hastelloy® C-22.

As can be seen in FIG. 5 an increase in temperature to 50° C.-60° C. has a positive effect on the conversion of NMM. These tests were carried out without $CO_2$. With a further increase, the hydrogen peroxide at the reactor wall breaks down before it can react with NMM. The reaction product is brown-red and there is massive gas development. Hastelloy® C-22 without metal masker is rather poorly suitable as reactor material for this reaction. Since the reaction progresses without difficulty in high-grade steels of class 1.43, 1.44 and 1.45, a possible reason for this is the high proportion of molybdenum and/or nickel, which catalyses the breakdown of hydrogen peroxide. The material Hastelloy® C-22 is preferably not used in accordance with the invention, or is masked.

Non-rusting, corrosion-resistant steels, austenitic steels of steel group numbers 1.40xx to 1.45xx are preferred capillary tube materials.

Precious metals, such as gold/platinum, or the transition metals titanium/tantalum and a wide range of different polymers, such as PEEK, PTFE, PFA, PVDF, PMMA, PVC, PET are likewise outstandingly suitable as reactor materials, such as hollow bodies, in particular capillaries, tubes and mixing plates, as isolated material or in combinations, for carrying out this reaction. Used hollow body, tube and capillary materials can also be used coated or enamelled.

TABLE 5

Parameters for testing the phosphoric acid addition

| A Material | B Temperature [° C.] | C Reactant 1 N-methylmorpholine (NMM) [ml/min] | D Reactant 2 hydrogen peroxide (H2O2) [ml/min] | E Molar ratio reactant 1:reactant 2 [mol/mol] | F CO2 in NMM [mass %] | G Concentration H2O2 [mass %] | H CO2 in H2O2 [mass %] | I H3PO4 in H2O2 [mass %] | J Pressure [bar] | K Throughput [ml/min] | L Conversion [%] | N Fluid speed [m/min] | O Hydrodynamic residence time in the reaction region reactor length [min] | P Reactor-specific surface load [l/m²h] | Q Reactor-specific volume load [l/m³h] | R Surface:volume ratio |
|---|---|---|---|---|---|---|---|---|---|---|---|---|---|---|---|---|
| Hastelloy ® C-22 | 30 | 0.18 | 0.16 | 1:1 | 0 | 32 | 0 | 0 | 6.89 | 0.34 | 40 | 0.43 | 12.13 | 1.24 | 4,947.59 | 4 |
| | 30 | 0.27 | 0.23 | 1:1 | 0 | 32 | 0 | 0 | 6.89 | 0.5 | 48 | 0.64 | 8.25 | 1.82 | 7,275.87 | 4 |
| | 30 | 0.54 | 0.47 | 1:1 | 0 | 32 | 0 | 0 | 6.89 | 1.01 | 55 | 1.29 | 4.08 | 3.67 | 14,697.26 | 4 |
| | 50 | 0.18 | 0.16 | 1:1 | 0.5 | 32 | 0 | 0 | 6.89 | 0.34 | 73 | 0.43 | 12.13 | 1.24 | 4,947.59 | 4 |
| | 50 | 0.27 | 0.23 | 1:1 | 0 | 32 | 0 | 0 | 6.89 | 0.5 | 67 | 0.64 | 8.25 | 1.82 | 7,275.87 | 4 |
| | 50 | 0.54 | 0.47 | 1:1 | 0 | 32 | 0 | 0 | 6.89 | 1.01 | 43 | 1.29 | 4.08 | 3.67 | 14,697.26 | 4 |
| | 60 | 0.18 | 0.16 | 1:1 | 0 | 29 | 0 | 0 | 6.89 | 0.34 | 8 | 0.43 | 12.13 | 1.24 | 4,947.59 | 4 |
| | 60 | 0.27 | 0.23 | 1:1 | 0 | 29 | 0 | 0 | 6.89 | 0.5 | 18 | 0.64 | 8.25 | 1.82 | 7,275.87 | 4 |
| | 60 | 0.54 | 0.47 | 1:1 | 0 | 29 | 0 | 0 | 6.89 | 1.01 | 12 | 1.29 | 4.08 | 3.67 | 14,697.26 | 4 |
| | 70 | 0.18 | 0.16 | 1:1 | 0 | 29 | 0 | 0 | 6.89 | 0.34 | 59 | 0.43 | 12.13 | 1.24 | 4,947.59 | 4 |
| | 70 | 0.27 | 0.23 | 1:1 | 0 | 29 | 0 | 0 | 6.89 | 0.5 | 31 | 0.64 | 8.25 | 1.82 | 7,275.87 | 4 |
| | 70 | 0.54 | 0.47 | 1:1 | 0 | 29 | 0 | 0 | 6.89 | 1.01 | 22 | 1.29 | 4.08 | 3.67 | 14,697.26 | 4 |
| | 80 | 0.18 | 0.16 | 1:1 | 0 | 29 | 0 | 0 | 6.89 | 0.34 | 86 | 0.43 | 12.13 | 1.24 | 4,947.59 | 4 |
| | 80 | 0.27 | 0.23 | 1:1 | 0 | 29 | 0 | 0 | 6.89 | 0.5 | 89 | 0.64 | 8.25 | 1.82 | 7,275.87 | 4 |
| | 80 | 0.54 | 0.47 | 1:1 | 0 | 29 | 0 | 0 | 6.89 | 1.01 | 87 | 1.29 | 4.08 | 3.67 | 14,697.26 | 4 |

45

TABLE 6

Parameters for the CO$_2$ addition

| A Material | B Temperature [° C.] | C Reactant 1 N-methylmorpholine (NMM) [ml/min] | D Reactant 2 hydrogen peroxide (H2O2) [ml/min] | E Molar ratio reactant 1:reactant 2 [mol/mol] | F CO2 in NMM [mass %] | G Concentration H2O2 [mass %] | H CO2 in H2O2 [mass %] | I H3PO4 in H2O2 [mass %] |
|---|---|---|---|---|---|---|---|---|
| 1.4404 | 60 | 2.7 | 2.42 | 1:1.1 | 0.5 | 29 | 0 | 0 |
| | 60 | 2 | 1.79 | 1:1.1 | 0.5 | 29 | 0 | 0 |
| | 60 | 1.6 | 1.43 | 1:1.1 | 0.5 | 29 | 0 | 0 |
| | 60 | 0.8 | 0.72 | 1:1.1 | 0.5 | 29 | 0 | 0 |
| | 60 | 0.5 | 0.45 | 1:1.1 | 0.5 | 32 | 0 | 0 |
| | 60 | 4 | 3.58 | 1:1.1 | 0.5 | 32 | 0 | 0.1 |
| | 60 | 2.7 | 2.42 | 1:1.1 | 0.5 | 29 | 0 | 0.1 |
| | 60 | 2 | 1.79 | 1:1.1 | 0.5 | 29 | 0 | 0.1 |
| | 60 | 0.8 | 0.72 | 1:1.1 | 0.5 | 29 | 0 | 0.1 |
| | 60 | 0.5 | 0.45 | 1:1.1 | 0.5 | 29 | 0 | 0.1 |

TABLE 6-continued

Parameters for the $CO_2$ addition

| J Pressure [bar] | K Throughput [ml/min] | L Conversion [%] | M Yield NMMO [%] | N Fluid speed [m/min] | O Hydrodynamic residence time in the reaction region reactor length [min] | P Reactor-specific surface load [l/m²h] | Q Reactor-specific volume load [l/m³h] | R Surface:volume ratio |
|---|---|---|---|---|---|---|---|---|
| 20 | 5.12 | 84 | 75 | 6.52 | 0.69 | 21.73 | 86,922.38 | 4 |
| 20 | 3.79 | 86 | 75 | 4.83 | 0.93 | 16.09 | 64,342.94 | 4 |
| 20 | 3.03 | 86 | 74 | 3.86 | 1.17 | 1.17 | 51,440.39 | 4 |
| 20 | 1.52 | 87 | 74 | 1.94 | 2.33 | 2.33 | 25,805.08 | 4 |
| 20 | 0.95 | 83 | 81 | 1.21 | 3.72 | 3.72 | 16,128.18 | 4 |
| 20 | 7.58 | 69 | 68 | 9.65 | 0.47 | 0.47 | 128,685.87 | 4 |
| 20 | 5.12 | 83 | 81 | 6.52 | 0.69 | 0.69 | 86,922.38 | 4 |
| 20 | 3.79 | 90 | 90 | 4.83 | 0.93 | 0.93 | 64,342.94 | 4 |
| 20 | 1.52 | 92 | 90 | 1.94 | 2.33 | 2.33 | 25,805.08 | 4 |
| 20 | 0.95 | 91 | 90 | 1.21 | 3.72 | 3.72 | 16,128.18 | 4 |

Influence of the $CO_2$ Concentration on the Reaction Speed

The positive effect of the addition of $CO_2$ on the reaction solution will be examined in greater detail. In order to quantify, tests were performed with different % by weight $CO_2$ (dissolved and in relation to the amine). As can be seen in FIG. 7, the reaction speed rises significantly with the dissolved % by weight. Parameters and results are shown in Table 6.

Influence of Temperature on the Progress of the Reaction

In order to achieve the highest possible reaction speed, yet still selective reaction, tests were performed at 40-70° C. (FIG. 8). With temperatures up to 60° C., the conversion and the yield of NMM increase massively. However, the yield reduces at 70° C., which indicates a runaway of the reaction and therefore a decomposition of the reactants and also the product between 60 and 70° C. In contrast to a discontinuous operating method, the continuous method according to the invention allows an exact temperature control with larger production amounts, and therefore the temperature-control temperatures can be effectively maintained also in the reaction fluid. Parameters and results are shown in Table 7.

Influence of the Concentration of the Hydrogen Peroxide on the Production Rate

Figure 9:
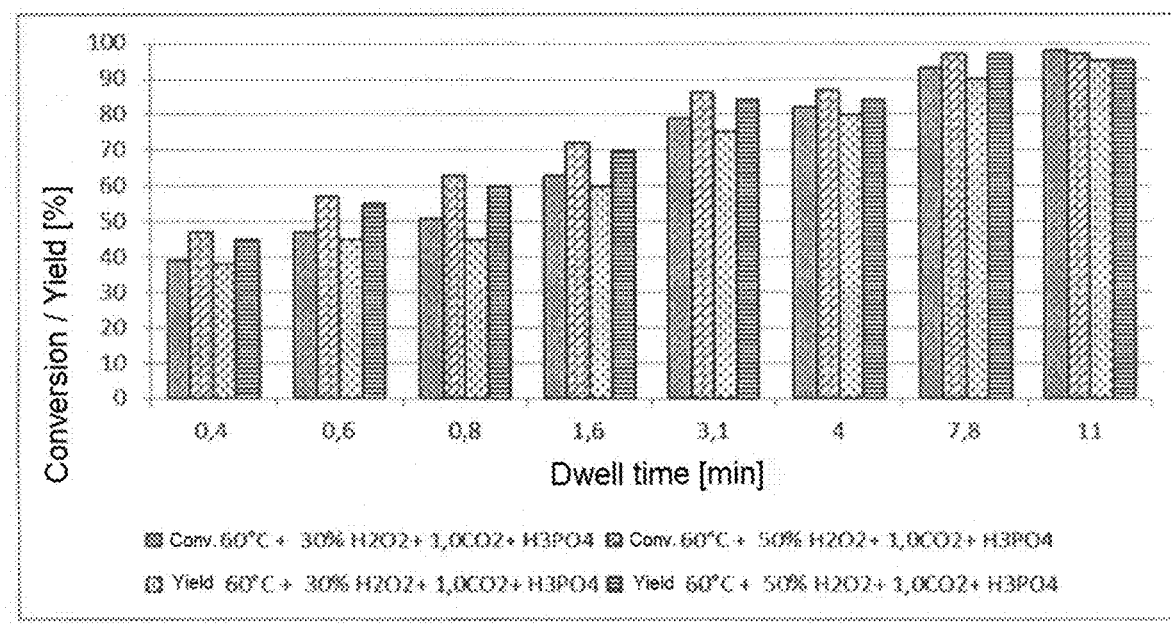
FIG. 9 shows the influence of the concentration of the hydrogen peroxide on the production rate.

In order to determine which concentration of hydrogen peroxide in the reaction solution is expedient, identical tests were performed with 30 and with 50% by weight hydrogen peroxide (FIG. 9). The use of 50% by weight hydrogen peroxide proved to be more favourable. In addition, more highly concentrated NMMNO can be obtained in this way. The advantage of the microreaction system according to the invention is that the use of very concentrated hydrogen peroxide poses no problem in respect of the heat of reaction. Parameters and results are shown in Table 8.

TABLE 7

Temperature variations

| A Material | B Temperature [° C.] | C Reactant 1 N-methylmorpholine (NMM) [ml/min] | D Reactant 2 hydrogen peroxide (H2O2) [ml/min] | E Molar ratio reactant 1:reactant 2 [mol/mol] | F CO2 in NMM [mass %] | G Concentration H2O2 [mass %] | H CO2 in H2O2 [mass %] | I H3PO4 in H2O2 [mass %] |
|---|---|---|---|---|---|---|---|---|
| 1.4404 | 40 | 4.8 | 2.71 | 1:1.1 | 1 | 30 | 0 | 0.1 |
| | 40 | 3.2 | 1.81 | 1:1.1 | 1 | 30 | 0 | 0.1 |
| | 40 | 2.4 | 1.36 | 1:1.1 | 1 | 30 | 0 | 0.1 |
| | 40 | 1.2 | 0.68 | 1:1.1 | 1 | 30 | 0 | 0.1 |
| | 40 | 0.6 | 0.34 | 1:1.1 | 1 | 30 | 0 | 0.1 |
| | 40 | 0.47 | 0.27 | 1:1.1 | 1 | 30 | 0 | 0.1 |
| | 40 | 0.24 | 0.14 | 1:1.1 | 1 | 30 | 0 | 0.1 |
| | 50 | 4.8 | 2.71 | 1:1.1 | 1 | 30 | 0 | 0.1 |
| | 50 | 3.2 | 1.81 | 1:1.1 | 1 | 30 | 0 | 0.1 |
| | 50 | 2.4 | 1.36 | 1:1.1 | 1 | 30 | 0 | 0.1 |
| | 50 | 1.2 | 0.68 | 1:1.1 | 1 | 30 | 0 | 0.1 |
| | 50 | 0.6 | 0.34 | 1:1.1 | 1 | 30 | 0 | 0.1 |
| | 50 | 0.47 | 0.27 | 1:1.1 | 1 | 30 | 0 | 0.1 |
| | 50 | 0.24 | 0.14 | 1:1.1 | 1 | 30 | 0 | 0.1 |
| | 60 | 4.8 | 2.71 | 1:1.1 | 1 | 30 | 0 | 0.1 |
| | 60 | 3.2 | 1.81 | 1:1.1 | 1 | 30 | 0 | 0.1 |
| | 60 | 2.4 | 1.36 | 1:1.1 | 1 | 30 | 0 | 0.1 |
| | 60 | 1.2 | 0.68 | 1:1.1 | 1 | 30 | 0 | 0.1 |
| | 60 | 0.6 | 0.34 | 1:1.1 | 1 | 30 | 0 | 0.1 |
| | 60 | 0.47 | 0.27 | 1:1.1 | 1 | 30 | 0 | 0.1 |
| | 60 | 0.24 | 0.14 | 1:1.1 | 1 | 30 | 0 | 0.1 |
| | 70 | 4.8 | 2.71 | 1:1.1 | 1 | 30 | 0 | 0.1 |

TABLE 7-continued

Temperature variations

| | | | | | | | | |
|---|---|---|---|---|---|---|---|---|
| | 70 | 3.2 | 1.81 | 1:1.1 | 1 | 30 | 0 | 0.1 |
| | 70 | 2.4 | 1.36 | 1:1.1 | 1 | 30 | 0 | 0.1 |
| | 70 | 1.2 | 0.68 | 1:1.1 | 1 | 30 | 0 | 0.1 |
| | 70 | 0.6 | 0.34 | 1:1.1 | 1 | 30 | 0 | 0.1 |
| | 70 | 0.47 | 0.27 | 1:1.1 | 1 | 30 | 0 | 0.1 |
| | 70 | 0.24 | 0.14 | 1:1.1 | 1 | 30 | 0 | 0.1 |

| J Pressure [bar] | K Throughput [ml/min] | L Conversion [%] | M Yield NMMO [%] | N Fluid speed [m/min] | O Hydrodynamic residence time in the reaction region reactor length [min] | P Reactor-specific surface load [l/m$^2$h] | Q Reactor-specific volume load [l/m$^3$h] | R Surface:volume ratio |
|---|---|---|---|---|---|---|---|---|
| 20 | 7.51 | 21 | 18 | 9.56 | 0.39 | 38.25 | 152,996.98 | 4 |
| 20 | 5.01 | 27 | 26 | 6.38 | 0.59 | 25.52 | 102,065.89 | 4 |
| 20 | 3.76 | 32 | 29 | 4.79 | 0.78 | 19.15 | 76,600.35 | 4 |
| 20 | 1.88 | 38 | 37 | 2.39 | 1.57 | 9.58 | 38,300.18 | 4 |
| 20 | 0.94 | 52 | 50 | 1.20 | 3.13 | 4.79 | 19,150.09 | 4 |
| 20 | 0.74 | 57 | 55 | 0.94 | 3.98 | 3.77 | 15,075.60 | 4 |
| 20 | 0.38 | 82 | 78 | 0.48 | 7.75 | 1.94 | 7,741.52 | 4 |
| 20 | 7.51 | 30 | 30 | 9.56 | 0.39 | 38.25 | 152,996.98 | 4 |
| 20 | 5.01 | 38 | 18 | 6.38 | 0.59 | 25.52 | 102,065.89 | 4 |
| 20 | 3.76 | 43 | 42 | 4.79 | 0.78 | 19.15 | 76,600.35 | 4 |
| 20 | 1.88 | 52 | 50 | 2.39 | 1.57 | 9.58 | 38,300.18 | 4 |
| 20 | 0.94 | 69 | 68 | 1.20 | 3.13 | 4.79 | 19,150.09 | 4 |
| 20 | 0.74 | 73 | 70 | 0.94 | 3.98 | 3.77 | 15,075.60 | 4 |
| 20 | 0.38 | 90 | 90 | 0.48 | 7.75 | 1.94 | 7,741.52 | 4 |
| 20 | 7.51 | 82 | 80 | 9.56 | 0.39 | 38.25 | 152,996.98 | 4 |
| 20 | 5.01 | 83 | 83 | 6.38 | 0.59 | 25.52 | 102,065.89 | 4 |
| 20 | 3.76 | 86 | 85 | 4.79 | 0.78 | 19.15 | 76,600.35 | 4 |
| 20 | 1.88 | 84 | 85 | 2.39 | 1.57 | 9.58 | 38,300.18 | 4 |
| 20 | 0.94 | 90 | 90 | 1.20 | 3.13 | 4.79 | 19,150.09 | 4 |
| 20 | 0.74 | 88 | 87 | 0.94 | 3.98 | 3.77 | 15,075.60 | 4 |
| 20 | 0.38 | 96 | 85 | 0.48 | 7.75 | 1.94 | 7,741.52 | 4 |
| 20 | 7.51 | 35 | 30 | 9.56 | 0.39 | 38.25 | 152,996.98 | 4 |
| 20 | 5.01 | 25 | 22 | 6.38 | 0.59 | 25.52 | 102,065.89 | 4 |
| 20 | 3.76 | 28 | 15 | 4.79 | 0.78 | 19.15 | 76,600.35 | 4 |
| 20 | 1.88 | 25 | 23 | 2.39 | 1.57 | 9.58 | 38,300.18 | 4 |
| 20 | 0.94 | 33 | 24 | 1.20 | 3.13 | 4.79 | 19,150.09 | 4 |
| 20 | 0.74 | 28 | 22 | 0.94 | 3.98 | 3.77 | 15,075.60 | 4 |
| 20 | 0.38 | 25 | 16 | 0.48 | 7.75 | 1.94 | 7,741.52 | 4 |

TABLE 8

Parameters for $H_2O_2$ addition

| A Material | B Temperature [°C.] | C Reactant 1 N-methylmorpholine (NMM) [ml/min] | D Reactant 2 hydrogen peroxide (H2O2) [ml/min] | E Molar ratio reactant 1:reactant 2 [mol/mol] | F CO2 in NMM [mass %] | G Concentration H2O2 [mass %] | H CO2 in H2O2 [mass %] | I H3PO4 in H2O2 [mass %] |
|---|---|---|---|---|---|---|---|---|
| 1.4404 | 60 | 4.8 | 2.71 | 1:1.1 | 1 | 30 | 0 | 0.1 |
| | 60 | 3.2 | 1.81 | 1:1.1 | 1 | 30 | 0 | 0.1 |
| | 60 | 2.4 | 1.36 | 1:1.1 | 1 | 30 | 0 | 0.1 |
| | 60 | 1.2 | 0.68 | 1:1.1 | 1 | 30 | 0 | 0.1 |
| | 60 | 0.6 | 0.34 | 1:1.1 | 1 | 30 | 0 | 0.1 |
| | 60 | 0.47 | 0.27 | 1:1.1 | 1 | 30 | 0 | 0.1 |
| | 60 | 0.24 | 0.14 | 1:1.1 | 1 | 30 | 0 | 0.1 |
| | 60 | 0.17 | 0.1 | 1:1.1 | 1 | 30 | 0 | 0.1 |
| | 60 | 4.8 | 2.71 | 1:1.1 | 1 | 50 | 0 | 0.1 |
| | 60 | 3.2 | 1.81 | 1:1.1 | 1 | 50 | 0 | 0.1 |
| | 60 | 2.4 | 1.36 | 1:1.1 | 1 | 50 | 0 | 0.1 |
| | 60 | 1.2 | 0.68 | 1:1.1 | 1 | 50 | 0 | 0.1 |
| | 60 | 0.6 | 0.34 | 1:1.1 | 1 | 50 | 0 | 0.1 |
| | 60 | 0.47 | 0.27 | 1:1.1 | 1 | 50 | 0 | 0.1 |
| | 60 | 0.24 | 0.14 | 1:1.1 | 1 | 50 | 0 | 0.1 |
| | 60 | 0.17 | 0.1 | 1:1.1 | 1 | 50 | 0 | 0.1 |
| | 60 | 4.8 | 2.71 | 1:1.1 | 0.5 | 50 | 0 | 0.1 |
| | 60 | 3.2 | 1.81 | 1:1.1 | 0.5 | 50 | 0 | 0.1 |

TABLE 8-continued

Parameters for H₂O₂ addition

| | | | | | | | |
|---|---|---|---|---|---|---|---|
| 60 | 2.4 | 1.36 | 1:1.1 | 0.5 | 50 | 0 | 0.1 |
| 60 | 1.2 | 0.68 | 1:1.1 | 0.5 | 50 | 0 | 0.1 |
| 60 | 0.6 | 0.34 | 1:1.1 | 0.5 | 50 | 0 | 0.1 |
| 60 | 0.47 | 0.27 | 1:1.1 | 0.5 | 50 | 0 | 0.1 |
| 60 | 0.24 | 0.14 | 1:1.1 | 0.5 | 50 | 0 | 0.1 |
| 60 | 0.17 | 0.1 | 1:1.1 | 0.5 | 50 | 0 | 0.1 |

| J Pressure [bar] | K Throughput [ml/min] | L Conversion [%] | M Yield NMMO [%] | N Fluid speed [m/min] | O Hydrodynamic residence time in the reaction region reactor length [min] | P Reactor-specific surface load [l/m²h] | Q Reactor-specific volume load [l/m³h] | R Surface:volume ratio |
|---|---|---|---|---|---|---|---|---|
| 20 | 7.51 | 39 | 38 | 9.56 | 0.39 | 38.2 | 152,997.0 | 4 |
| 20 | 5.01 | 47 | 45 | 6.38 | 0.59 | 25.5 | 102,065.9 | 4 |
| 20 | 3.76 | 51 | 45 | 4.79 | 0.78 | 19.2 | 76,600.4 | 4 |
| 20 | 1.88 | 63 | 60 | 2.39 | 1.57 | 9.6 | 38,300.2 | 4 |
| 20 | 0.94 | 79 | 75 | 1.20 | 3.13 | 4.8 | 19,150.1 | 4 |
| 20 | 0.74 | 82 | 80 | 0.94 | 3.98 | 3.8 | 15,075.6 | 4 |
| 20 | 0.38 | 93 | 90 | 0.48 | 7.75 | 1.9 | 7,741.5 | 4 |
| 20 | 0.27 | 98 | 95 | 0.34 | 10.91 | 1.4 | 5,500.6 | 4 |
| 20 | 7.51 | 47 | 45 | 4.79 | 0.39 | 38.2 | 152,997.0 | 4 |
| 20 | 5.01 | 57 | 55 | 2.39 | 0.59 | 25.5 | 102,065.9 | 4 |
| 20 | 3.76 | 63 | 60 | 1.20 | 0.78 | 19.2 | 76,600.4 | 4 |
| 20 | 1.88 | 72 | 70 | 0.94 | 1.57 | 9.6 | 38,300.2 | 4 |
| 20 | 0.94 | 86 | 84 | 0.48 | 3.13 | 4.8 | 19,150.1 | 4 |
| 20 | 0.74 | 87 | 84 | 0.34 | 3.98 | 3.8 | 15,075.6 | 4 |
| 20 | 0.38 | 97 | 97 | 4.79 | 7.75 | 1.9 | 7,741.5 | 4 |
| 20 | 0.27 | 97 | 95 | 2.39 | 10.91 | 1.4 | 5,500.6 | 4 |
| 20 | 7.51 | 38 | 34 | 4.79 | 0.39 | 38.2 | 152,997.0 | 4 |
| 20 | 5.01 | 34 | 33 | 2.39 | 0.59 | 25.5 | 102,065.9 | 4 |
| 20 | 3.76 | 54 | 53 | 1.20 | 0.78 | 19.2 | 76,600.4 | 4 |
| 20 | 1.88 | 60 | 42 | 0.94 | 1.57 | 9.6 | 38,300.2 | 4 |
| 20 | 0.94 | 70 | 69 | 0.48 | 3.13 | 4.8 | 19,150.1 | 4 |
| 20 | 0.74 | 81 | 80 | 0.34 | 3.98 | 3.8 | 15,075.6 | 4 |
| 20 | 0.38 | 90 | 90 | 4.79 | 7.75 | 1.9 | 7,741.5 | 4 |
| 20 | 0.27 | 99 | 95 | 2.39 | 10.91 | 1.4 | 5,500.6 | 4 |

Large-Scale Reactor

Further experiments with the same chemicals and similar test run-through as in the previous examples were carried out, only with a larger reactor.

The design of the larger reactor is similar to the above-described reactor design with the following changes. The length of the used tubes was 2.8 m with an inner diameter of from 1.5 to 4 mm, with and without pinch points. The number of used tubes was 40. The attained production capacity in this experiment was from 1 kg/h to 3 kg/h NMMNO based on 100% NMMNO. As a result of this production capacity it was necessary to install a cooler instead of the heating thermostat (see reactor diagram (2))—(Lauda: ECO SILVER RE415)).

1% by weight $CO_2$ was dissolved in NMM at a slight overpressure (0.3 bar), and the NMM/$CO_2$ was then transferred into the storage container (3). Now, 0.1% by weight $H_3PO_4$ was added to the $H_2O_2$ solution and emptied into the storage container (4). The rest of the approach was identical to the examples described above.

Figure 10:
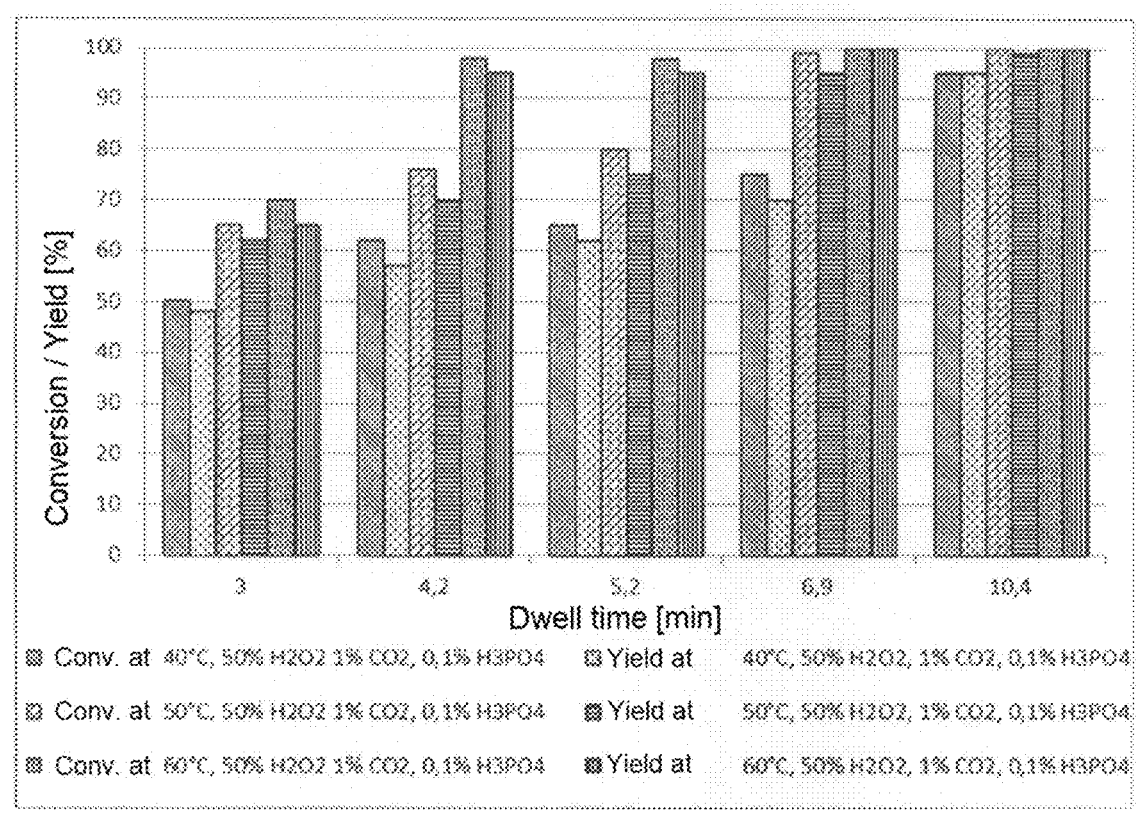
FIG. 10 shows results with a large-volume reactor.

In this experiment it was attempted to attain the highest possible production capacity by the larger reactor and by greater volume flow rates. Results are shown in FIG. 10 and in Table 9.

TABLE 9

Large-scale reactor

| A Material | B Temperature [° C.] | C Reactant 1 N-methylmorpholine (NMM) [ml/min] | D Reactant 2 hydrogen peroxide (H2O2) [ml/min] | E Molar ratio reactant 1:reactant 2 [mol/mol] | F CO2 in NMM [mass %] | G Concentration H2O2 [mass %] | H CO2 in H2O2 [mass %] | I H3PO4 in H2O2 [mass %] |
|---|---|---|---|---|---|---|---|---|
| 1.4404 | 40 | 117.3 | 66.0 | 1:1.0 | 1 | 50.75 | 0 | 0.1 |
| | 40 | 83.8 | 47.1 | 1:1.1 | 1 | 50.75 | 0 | 0.1 |
| | 40 | 67 | 37.7 | 1:1.1 | 1 | 50.75 | 0 | 0.1 |
| | 40 | 50.3 | 28.3 | 1:1.1 | 1 | 50.75 | 0 | 0.1 |
| | 40 | 33.5 | 18.8 | 1:1.1 | 1 | 50.75 | 0 | 0.1 |
| | 50 | 117.3 | 66.0 | 1:1.0 | 1 | 50.75 | 0 | 0.1 |
| | 50 | 83.8 | 47.1 | 1:1.1 | 1 | 50.75 | 0 | 0.1 |

TABLE 9-continued

Large-scale reactor

| 50 | 67 | 37.7 | 1:1.1 | 1 | 50.75 | 0 | 0.1 |
| 50 | 50.3 | 28.3 | 1:1.1 | 1 | 50.75 | 0 | 0.1 |
| 50 | 33.5 | 18.8 | 1:1.1 | 1 | 50.75 | 0 | 0.1 |
| 60 | 117.3 | 66.0 | 1:1.0 | 1 | 50.75 | 0 | 0.1 |
| 60 | 83.8 | 47.1 | 1:1.1 | 1 | 50.75 | 0 | 0.1 |
| 60 | 67 | 37.7 | 1:1.1 | 1 | 50.75 | 0 | 0.1 |
| 60 | 50.3 | 28.3 | 1:1.1 | 1 | 50.75 | 0 | 0.1 |
| 60 | 33.5 | 18.8 | 1:1.1 | 1 | 50.75 | 0 | 0.1 |

| J Pressure [bar] | K Throughput [ml/min] | L Conversion [%] | M Yield NMMO [%] | N Fluid speed [m/min] | O Hydrodynamic residence time in the reaction region reactor length [min] | P Reactor-specific surface load [l/m²h] | Q Reactor-specific volume load [l/m³h] | R Surface:volume ratio |
|---|---|---|---|---|---|---|---|---|
| 103 | 183.3 | 50 | 48 | 103.7 | 0.8 | 56.87 | 74445 | 1.5-4 mm used. This corresponds to a reduction of the surface:volume ratio from 2.7 to 1 over the reactor length, wherein it is sure to be >2 up to conversions of 50%. |
| 68 | 130.9 | 62 | 57 | 74.1 | 1.1 | 40.61 | 53163 | |
| 55 | 104.7 | 65 | 62 | 59.2 | 1.4 | 32.48 | 42523 | |
| 43 | 78.6 | 75 | 70 | 44.5 | 1.9 | 24.39 | 31922 | |
| 34 | 52.3 | 95 | 95 | 29.6 | 2.8 | 16.23 | 21241 | |
| 95 | 183.3 | 65 | 62 | 103.7 | 0.8 | 56.87 | 74445 | |
| 65 | 130.9 | 76 | 70 | 74.1 | 1.1 | 40.61 | 53163 | |
| 52 | 104.7 | 80 | 75 | 59.2 | 1.4 | 32.48 | 42523 | |
| 46 | 78.6 | 99 | 95 | 44.5 | 1.9 | 24.39 | 31922 | |
| 32 | 52.3 | 100 | 99 | 29.6 | 2.8 | 16.23 | 21241 | |
| 92 | 183.3 | 70 | 65 | 103.7 | 0.8 | 56.87 | 74445 | |
| 65 | 130.9 | 98 | 95 | 74.1 | 1.1 | 40.61 | 53163 | |
| 50 | 104.7 | 98 | 95 | 59.2 | 1.4 | 32.48 | 42523 | |
| 41 | 78.6 | 100 | 100 | 44.5 | 1.9 | 24.39 | 31922 | |
| 28 | 52.3 | 100 | 100 | 29.6 | 2.8 | 16.23 | 21241 | |

Reaction System According to FIG. 11

$CO_2$ Saturation Directly in the Microreactor

The test was carried out as described above with the small reactor, with the difference that the reactant 1 99% undiluted NMM was conveyed via a computer-controlled pump (5) from the storage container (3) into the microreactor (1) and was temperature-controlled to 20° C. using cooling water. The maximum soluble gas volume, which was determined from the solubility tests, was conducted via a metering valve (14) from the gas bottle (15) into the microreactor. The pressure in the portion of the $CO_2$ saturation was controlled to [A] bar.

Two ECO SILVER RE415 heating thermostats (2, 16) from the company Lauda were used to control the temperature of the microreactor to T1=20° C. or T2=65° C. A mixture of water/ethylene glycol in a volume ratio 1:1 was used as cooling and heating medium.

In the hydrogen peroxide storage container (4), the reactant 2, hydrogen peroxide, was mixed with 0.1% by weight $H_3PO_4$, stored, and conveyed with a pump (6) into the microreactor (1). After the saturation tube (7) and preheating tube (8), the reactants were combined via a mixing module T3 (9). A static mixer (for example mixing plate) was used in the mixing module, as per WO 2010/055034. The reaction mixture was then conducted into the reaction tubes (10), where the reaction then took place. In order to increase the pressure in the reactor, a pressure-sustaining valve (11) with 20 bar was used after the reactor outlet. The incorporation of the pressure-sustaining valve was intended to suppress the decomposition and secondary reactions to the greatest possible extent, since there is a development of gas during the course of these undesirable reactions.

The desired product was collected, after an infrared measurement (13), in a vessel with agitator (12). Excess hydrogen peroxide was destroyed by guiding the reaction solution over immobilised $MnO_2$.

TABLE 10

Reactants of the separate $CO_2$ feed:

| | Reactant 1 | Reactant 2 | Reactant 3 |
|---|---|---|---|
| Volume flow | [B] ml/min | [C] ml/min | [D] % by weight based on reactant 1 |
| Molar ratio | | 1:1.1 | |
| Composition | 99 vol. % N-methylmorpholine | 50% by weight hydrogen peroxide with 0.1% by weight $H_3PO_4$ | $CO_2$ |

Figure 12:
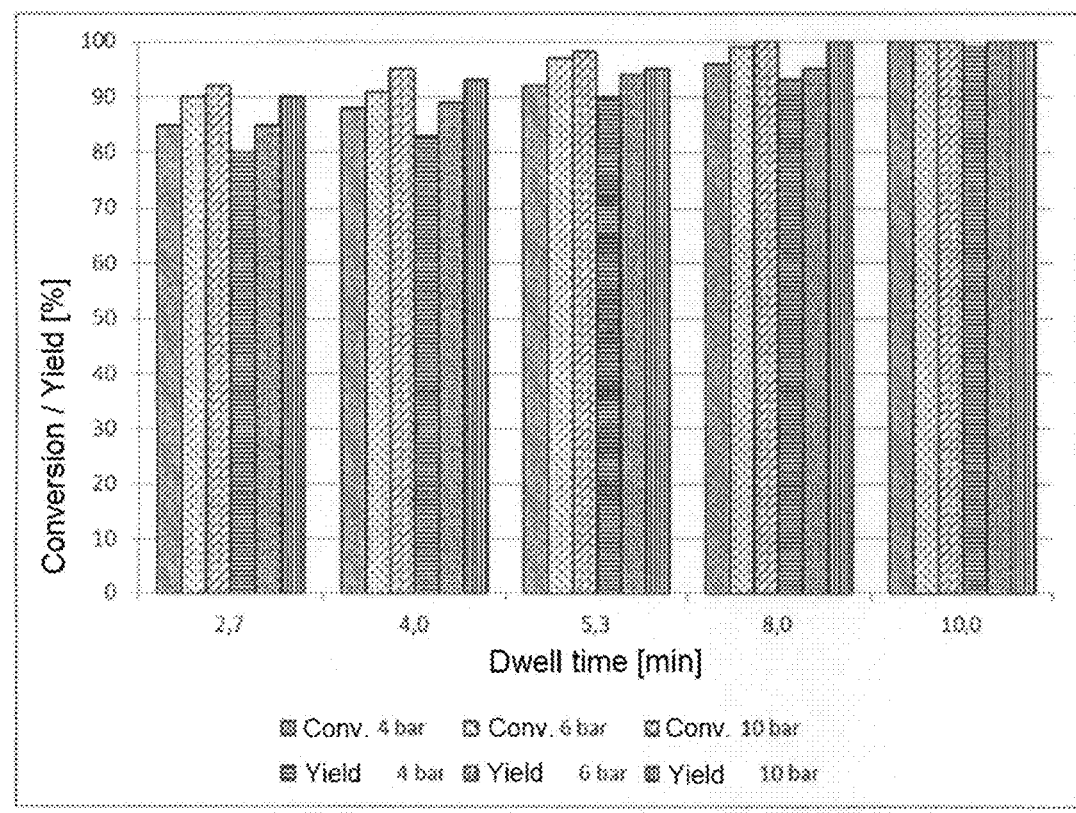
FIG. 12 shows results for separate $CO_2$ feed.

Throughputs of [E] ml/min with conversions of [F] % and yields of [G] % could be achieved. Results are shown in FIG. 12 and Tab. 12.

TABLE 11

| Parameters and units: | |
|---|---|
| Fluid speed | [H] m/min |
| Hydrodynamic residence time in the reaction region | [I] min |
| Reactor-specific surface load | [J] L/m²h |
| Reactor-specific volume load | [K] L/m³h |
| Surface:volume ratio | [L] |

TABLE 12

Results of the separate $CO_2$ feed:

| A Pressure in the saturation portion [bar] | B Reactant 1 N-methyl-morpholine (NMM) [ml/min] | C Reactant 2 hydrogen peroxide (H2O2) [ml/min] | D CO2 in NMM [mass %] | E Through-put [ml/min] | F Conversion [%] | G Yield NMMO [%] | H mx. fluid speed [m/min] | I Hydrodynamic residence time in the reaction region [min] | J Reactor-specific surface load [l/m²h] | K Reactor-specific volume load [l/m³h] | L Surface:volume ratio |
|---|---|---|---|---|---|---|---|---|---|---|---|
| 4 | 5.03 | 2.83 | 5 | 7.86 | 85 | 80 | 10.0 | 2.7 | 5.56 | 22457 | 4 |
| 4 | 3.35 | 1.88 | 5 | 5.23 | 88 | 83 | 6.7 | 4.0 | 3.70 | 14943 | 4 |
| 4 | 2.51 | 1.41 | 5 | 3.92 | 92 | 90 | 5.0 | 5.3 | 2.77 | 11200 | 4 |
| 4 | 1.68 | 0.9 | 5 | 2.6 | 96 | 93 | 3.3 | 8.0 | 1.85 | 7486 | 4 |
| 4 | 1.34 | 0.75 | 5 | 2.09 | 100 | 99 | 2.7 | 10.0 | 1.48 | 5971 | 4 |
| 6 | 5.03 | 2.83 | 7.5 | 7.86 | 90 | 85 | 10.0 | 2.7 | 5.56 | 22457 | 4 |
| 6 | 3.35 | 1.88 | 7.5 | 5.23 | 91 | 89 | 6.7 | 4.0 | 3.70 | 14943 | 4 |
| 6 | 2.51 | 1.41 | 7.5 | 3.92 | 97 | 94 | 5.0 | 5.3 | 2.77 | 11200 | 4 |
| 6 | 1.68 | 0.9 | 7.5 | 2.6 | 99 | 95 | 3.3 | 8.0 | 1.85 | 7486 | 4 |
| 6 | 1.34 | 0.75 | 7.5 | 2.09 | 100 | 100 | 2.7 | 10.0 | 1.48 | 5971 | 4 |
| 10 | 5.03 | 2.83 | 14 | 7.86 | 92 | 90 | 10.0 | 2.7 | 5.56 | 22457 | 4 |
| 10 | 3.35 | 1.88 | 14 | 5.23 | 95 | 93 | 6.7 | 4.0 | 3.70 | 14943 | 4 |
| 10 | 2.51 | 1.41 | 14 | 3.92 | 98 | 95 | 5.0 | 5.3 | 2.77 | 11200 | 4 |
| 10 | 1.68 | 0.9 | 14 | 2.6 | 100 | 100 | 3.3 | 8.0 | 1.85 | 7486 | 4 |
| 10 | 1.34 | 0.75 | 14 | 2.09 | 100 | 100 | 2.7 | 10.0 | 1.48 | 5971 | 4 |

The invention claimed is:

1. A method for producing an amine oxide, comprising: oxidation of a tertiary amine in a reactor with an elongate hollow body, under continuous introduction of tertiary amine in a reaction fluid and export of amine oxide, wherein
   i) a surface-to-volume ratio of 0.5 m²/m³ or more is provided in the hollow body, at least over a length of the hollow body in which the amine is oxidised to an extent of 50 mol %;
   ii) a specific surface load of 1 l/m²h to 40 l/m²h is provided in the hollow body; and/or
   iii) a specific volume load of 1,000 l/m³h to 30,000 l/m³h is provided in the hollow body; and
   wherein
   the reaction fluid is guided in the hollow body with a laminar flow.

2. The method according to claim 1, characterised in that the tertiary amine is used in a molar ratio of 1:0.9 to 1:1.3 to hydrogen peroxide as oxidant.

3. The method according to claim 1, characterised in that the amine oxide is N-methylmorpholine N-oxide and the tertiary amine is N-methylmorpholine.

4. The method according to claim 1, characterised in that a flow velocity of the reaction fluid in the hollow body is set to a residence time of the tertiary amine of 0.4 minutes to 14 minutes.

5. The method according to claim 1, characterised in that the flow velocity of the reaction fluid is 0.1 m/min to 200 m/min.

6. The method according to claim 1, characterised in that the reaction fluid temperature in the hollow body is 20° C. to 70° C.

7. The method according to claim 1, characterised in that the pressure in the hollow body is 1 bar to 200 bar.

8. The method according to claim 1, characterised in that the inner diameter of a hollow body of the reactor is 0.25 mm to 10 mm.

9. The method according to claim 1, characterised in that the length of a hollow body of the reactor is 0.5 m to 20 m.

10. The method according to claim 1, characterized in that an inner wall of the hollow body of the reactor contains one or more metals, wherein the inner wall of the hollow body is made of austenitic steel.

11. The method according to claim 1, characterised in that the tertiary amine is fed into the hollow body in a concentration of 40 vol. % to 100 vol. %.

12. The method according to claim 1, characterised in that an oxidant is fed into the hollow body in a concentration of 5% by weight to 80% by weight.

13. The method according to claim 1, characterised in that the reaction fluid is conveyed through the hollow body at a Bodenstein number of greater than 10, according to the formula $$Bo = u*L/D_{ax},$$

in which Bo is the Bodenstein number, u is the flow velocity of the reaction fluid, L is the length of the hollow body, and $D_{ax}$ is the axial dispersion flow of the reaction fluid.

14. The method according to claim 1, characterised in that $CO_2$ is fed into the hollow body in an amount of 0.5% by weight to 20% by weight, in relation to the tertiary amine.

15. The method according to claim 1, characterised in that a metal complexing agent, is added to the reaction fluid in an amount of 0.01% by weight to 3% by weight.

16. The method according to claim 1, characterised in that the oxidation of the tertiary amine is performed with an oxidant and excess oxidant is broken down or removed.

17. The method according to claim 1, characterised in that the amine oxide is brought to a concentration suitable for the dissolution of cellulose.

18. The method according to claim 1, characterised in that the reaction fluid is guided in a flow through the hollow body at a Reynolds number of 2300 or less.

19. The method according to claim 17, characterised in that the cellulose is dissolved in the amine oxide.

20. The method according to claim 19, characterised in that the dissolved cellulose is shaped into continuous shaped bodies and the cellulose of the shaped bodies is precipitated.

\* \* \* \* \*